US009314408B2

(12) United States Patent
Blomker et al.

(10) Patent No.: US 9,314,408 B2
(45) Date of Patent: Apr. 19, 2016

(54) DENTAL COMPOSITE MATERIALS COMPRISING TRICYCLIC PLASTICIZERS

(71) Applicant: VOCO Gmbh, Cuxhaven (DE)

(72) Inventors: Tobias Blomker, Hamburg (DE); Nils Fontein, Cuxhaven (DE); Manfred Stepputtis, Kutenholz (DE); Manfred Thomas Plaumann, Cuxhaven (DE)

(73) Assignee: Voco GmbH, Cuxhaven (DE)

( * ) Notice: Subject to any disclaimer, the term of this patent is extended or adjusted under 35 U.S.C. 154(b) by 277 days.

(21) Appl. No.: 13/757,366

(22) Filed: Feb. 1, 2013

(65) Prior Publication Data
US 2013/0203884 A1 Aug. 8, 2013

(30) Foreign Application Priority Data

Feb. 2, 2012 (DE) .......................... 10 2012 001 978

(51) Int. Cl.
A61K 6/08 (2006.01)
A61K 6/00 (2006.01)
A61K 6/083 (2006.01)

(52) U.S. Cl.
CPC ............... *A61K 6/0047* (2013.01); *A61K 6/083* (2013.01)

(58) Field of Classification Search
CPC ... A61K 6/0047; A61K 6/0052; A61K 6/083; A61K 6/08; A61K 6/087
See application file for complete search history.

(56) References Cited

U.S. PATENT DOCUMENTS

| | | | |
|---|---|---|---|
| 2,817,673 A | 12/1957 | Roelen et al. | |
| 4,323,348 A * | 4/1982 | Schmitz-Josten | A61K 6/083 106/35 |
| 4,337,349 A * | 6/1982 | Orlowski | C08F 20/36 427/2.26 |
| 4,351,853 A * | 9/1982 | Jochum | A61K 6/083 204/157.93 |
| 4,379,695 A * | 4/1983 | Orlowski | C08F 20/36 106/35 |
| 4,390,717 A | 6/1983 | Ishikawa et al. | |
| 4,528,396 A | 7/1985 | Sanderson et al. | |
| 4,772,530 A | 9/1988 | Gottschalk et al. | |
| 4,874,450 A | 10/1989 | Gottschalk | |
| 4,954,414 A | 9/1990 | Adair et al. | |
| 5,009,597 A * | 4/1991 | Schaefer | 433/212.1 |
| 5,055,372 A | 10/1991 | Shanklin et al. | |
| 5,057,393 A | 10/1991 | Shanklin et al. | |
| 5,761,169 A | 6/1998 | Mine et al. | |
| 6,642,286 B2 | 11/2003 | Nakayama et al. | |
| 7,081,485 B2 | 7/2006 | Suh et al. | |
| 7,148,382 B2 | 12/2006 | Wolf et al. | |
| 7,601,767 B2 * | 10/2009 | Ruppert | A61K 6/0091 433/228.1 |
| 2006/0252845 A1 * | 11/2006 | Ruppert | A61K 6/0091 523/115 |
| 2007/0027229 A1 | 2/2007 | Moszner et al. | |
| 2008/0287644 A1 | 11/2008 | Hummel et al. | |
| 2009/0036565 A1 * | 2/2009 | Utterodt | A61K 6/0091 523/116 |
| 2011/0250558 A1 | 10/2011 | Maletz et al. | |

FOREIGN PATENT DOCUMENTS

| | | |
|---|---|---|
| DE | 934889 C | 11/1955 |
| DE | 1495520 A1 | 4/1969 |
| DE | 2823165 A1 | 11/1979 |
| DE | 3236026 A1 | 3/1984 |
| DE | 3246654 A1 | 6/1984 |
| DE | 2420351 C3 | 7/1987 |
| DE | 3703120 A1 | 1/1988 |
| DE | 3801511 C2 | 7/1989 |
| DE | 3941629 C2 | 6/1990 |
| DE | 3902417 A1 | 8/1990 |
| DE | 4231579 C2 | 3/1993 |
| DE | 4416857 C1 | 6/1995 |
| DE | 69017484 T2 | 7/1995 |
| DE | 19708294 A1 | 9/1997 |
| DE | 19754029 A1 | 6/1998 |
| DE | 19711514 B4 | 9/1998 |
| DE | 19903177 A1 | 7/2000 |
| DE | 19941738 B4 | 3/2001 |
| DE | 19961341 C2 | 6/2001 |
| DE | 69231737 T2 | 8/2001 |
| DE | 69801010 T2 | 3/2002 |
| DE | 10147125 A1 | 4/2002 |
| DE | 10119831 A1 | 10/2002 |
| DE | 10126476 A1 | 12/2002 |
| DE | 69033994 T2 | 11/2003 |
| DE | 10235990 A1 | 2/2004 |
| DE | 69725380 T2 | 8/2004 |
| DE | 10352263 A1 | 6/2005 |
| DE | 69921231 T2 | 10/2005 |
| DE | 60116142 T2 | 7/2006 |
| DE | 102006019092 A1 | 3/2007 |
| DE | 60029481 T2 | 7/2007 |
| DE | 102006050153 A1 | 5/2008 |

(Continued)

OTHER PUBLICATIONS

European Search Report from European Application No. 13000545.7, dated May 22, 2014.

(Continued)

*Primary Examiner* — Sanza McClendon

(74) *Attorney, Agent, or Firm* — Armstrong Teasdale LLP

(57) ABSTRACT

The present invention relates to dental polymerizable composite materials (curable dental compositions) comprising one or more plasticizers comprising a tricyclic structural element, to dental materials (polymers), obtainable by curing from the dental polymerizable composite materials comprising one or more plasticizers comprising a tricyclic structural element, to processes for producing a dental material and to dental curable composite materials for use in a therapeutic method in the production of a dental material.

21 Claims, No Drawings

(56) References Cited

FOREIGN PATENT DOCUMENTS

| | | |
|---|---|---|
| DE | 602004009552 T2 | 7/2008 |
| DE | 102008028306 A1 | 12/2009 |
| DE | 202010014676 U1 | 12/2010 |
| DE | 102009046251 A1 | 5/2011 |
| DE | 102010003884 A1 | 10/2011 |
| EP | 0007508 A2 | 2/1980 |
| EP | 0047902 A2 | 3/1982 |
| EP | 0057474 A2 | 8/1982 |
| EP | 0059451 A1 | 9/1982 |
| EP | 0073413 B1 | 3/1983 |
| EP | 0049631 B1 | 2/1984 |
| EP | 0023686 B1 | 10/1984 |
| EP | 0173567 A2 | 3/1986 |
| EP | 0184095 B1 | 6/1986 |
| EP | 0262629 B1 | 4/1988 |
| EP | 0366977 B1 | 5/1990 |
| EP | 1042273 B1 | 10/2000 |
| EP | 1194110 B1 | 4/2002 |
| EP | 0948955 B1 | 9/2003 |
| EP | 0980682 B1 | 11/2003 |
| EP | 1563821 B1 | 8/2005 |
| EP | 1236459 B1 | 11/2005 |
| EP | 1720506 B1 | 11/2006 |
| EP | 1112995 B1 | 4/2007 |
| EP | 1839640 A2 | 10/2007 |
| EP | 1978048 A1 | 10/2008 |
| EP | 2436363 A2 | 4/2012 |
| EP | 2436364 A2 | 4/2012 |
| EP | 2436365 A2 | 4/2012 |
| EP | 2436366 A2 | 4/2012 |
| EP | 2436668 A1 | 4/2012 |
| EP | 2450025 A1 | 5/2012 |
| GB | 1576080 A * | 10/1980 |
| JP | 59001556 A | 1/1984 |
| WO | 0078704 A1 | 12/2000 |
| WO | 0078853 A1 | 12/2000 |
| WO | 02092021 A1 | 11/2002 |
| WO | 02092023 A1 | 11/2002 |
| WO | 2009065873 A2 | 5/2009 |
| WO | 2011005822 A1 | 1/2011 |

OTHER PUBLICATIONS

Search Report for German Application No. 102012001978.5, dated Aug. 6, 2012.

* cited by examiner

DENTAL COMPOSITE MATERIALS COMPRISING TRICYCLIC PLASTICIZERS

CROSS-REFERENCE TO RELATED APPLICATIONS

This application claims priority to German Patent Application No. 102012001978.5, filed Feb. 2, 2012, which is herein incorporated by reference in its entirety.

BACKGROUND OF THE DISCLOSURE

The present invention relates to dental polymerizable composite materials (curable dental compositions) comprising one or more plasticizers comprising a tricyclic structural element, to dental materials (polymers), obtainable by curing the dental polymerizable composite materials comprising one or more plasticizers comprising a tricyclic structural element, to processes for producing a dental material and to dental curable composite materials for use in a therapeutic method in the production of a dental material.

The materials obtainable from the curable dental compositions are particularly suitable as filling materials, core build-up materials, temporary crown and bridge materials, luting cements, relining materials, conditioners, dental materials, modeling materials, base materials, covering compositions for gingiva protection, prosthetic materials, as materials for a temporary supraconstruction for a dental implant or of a core for a temporary supraconstruction, or as inlays, onlays and veneers.

According to the indication, the dental compositions can be used in forms ranging from thin flowing materials as far as thick pasty formulations. Dental compositions generally cure by free-radical means and comprise, as well as the crosslinkable monomers and the initiators/catalysts, also fillers and specific additives which assume quite different functions. As well as free-radical curing, there are also other forms of curing, for example drying in oral release or lacquer systems for production of a carrier for dental active ingredients, or the setting of an initially liquid wound dressing for protection of the mucous membrane.

A very specific additive in curable dental compositions is that of the organic substances which are chemically inert with respect to the reactive components, also called inert solvents or plasticizers. According to the field of use, structure and amount, the inert organic substances or plasticizers meet different requirements.

Plasticizers in polymerizable dental compositions are thus well known from the prior art.

Within the context of the present text the term "(meth) acryloyl" is understood to mean both "acryloyl" and "methacryloyl".

DE 101 47 125 A1 describes resin compositions for a soft base material. The components used to date for plasticization of a cured material in the resin compositions for a soft base material have been phthalate-based plasticizers; the publication proposes alternative plasticizers, since it is now known that phthalates, being endocrine disruptors, can possibly adversely affect the human body. The application discloses, as plasticizers, acid esters selected from the group consisting of trimellitic esters, fatty acid esters, acetic esters, maleic esters, fumaric esters and citric esters. Explicit mention is made of tri-2-ethylhexyl trimellitate, dimethyl adipate, dibutyl adipate, diisobutyl adipate, diisonorbornyl adipate, di-2-ethylhexyl adipate, diisodecyl adipate, diethylene glycol adipate, dibutyl diglycol adipate, di-2-ethylhexyl azelate, dimethyl sebacate, dibutyl sebacate, di-2-ethylhexyl sebacate, methyl acetylricinolate, epoxidized soyabean oil, glyceryl triacetate, 2-ethylhexyl acetate, dimethyl maleate, dibutyl maleate, di-2-ethylhexyl maleate, dibutyl fumarate, di-2-ethylhexyl fumarate, trimethyl citrate, triethyl citrate, tripropyl citrate and triisobutyl citrate.

Among these compounds, preference is given to diisobutyl adipate, diisobornyl adipate, dibutyl sebacate and tributyl citrate. These compounds can be used individually or in mixtures for production of a soft base material, and they are unable to act as endocrine disruptors in bodies of life forms. The amount of the plasticizer should be between 20 and 80% by weight based on the total mass of the soft base material. If the amount is below 20% by weight, the softness imparted to the composition after polymerization is insufficient; if the amount is more than 80% by weight, the composition becomes too soft for a soft base material.

The resin compositions are used in the form of powder/liquid, liquid/liquid or paste systems in different mixing ratios.

EP 1 194 110 B1 discloses two-component paste/paste systems as temporary crown and bridge materials, which are formulated in a mixing ratio of base paste to catalyst paste of 10:1. Such systems also comprise plasticizing additives. The polymerizable dental composition comprises plasticizers in amounts of 1 to 30% by weight, preferably 1 to 20% by weight and especially 1 to 15% by weight, based on the total mass of the constituents. Suitable plasticizers are polyethylene glycol derivatives, polypropylene glycols, low molecular weight polyesters, dibutyl phthalate, dioctyl phthalate, dinonyl phthalate, diphenyl phthalate, di(isononyl) adipate, tricresyl phosphate and silicone oils.

In the examples of this publication, 2,2-bis-4-(2-hydroxyethoxyphenyl) propane bisacetate is used as the plasticizer in the catalyst pastes.

DE 32 46 654 A1 describes non-adhesive dental impression materials. In these systems, the starter component of the impression materials is used together with plasticizers, and examples of suitable plasticizers are said to be phthalic esters, acylated citric esters, polyglycols, dibenzyltoluene or polyethoxylated sorbitan esters.

DE 101 26 476 A1 (or DE 102 35 990 A1) relates to N-alkylaziridino prepolymers which are used in dentistry for impression materials. The impression materials also comprise plasticizers. For instance, the publication describes plasticizers of the ester type, such as $C_{12}$-$C_{15}$-alkyl lactates, ethyl or butyl esters of citric acid or of acetylcitric acid, phthalic esters of longer branched alcohols such as bis(2-ethylhexyl) phthalate or phthalic polyesters, $C_2$ to $C_{18}$-dialkyl esters of $C_2$ to $C_6$-dicarboxylic acids, such as bis(2-ethylhexyl) adipate, dioctyl malate, diisopropyl adipate, aromatic and aliphatic sulfonic esters, such as $C_2$ to $C_{20}$-alkylsulfonic esters of phenol or of $C_1$ to $C_{18}$-alkanols and typical aromatic plasticizers such as polyphenyls, dibenzyltoluene, and isomer mixtures of $C_{20}$ to $C_{30}$ aromatics. It is said to be preferable to use mixtures of plasticizers of the ester type and of the aromatic type. A preferred mixture is a mixture of acetyl tributyl citrate and dibenzyltoluene.

The patent application additionally specifies plasticizers having molar masses exceeding 2000 g/mol. These plasticizers include different types of compounds, such as polyethers, polyesters, polycarbonates, polyolefins, in which the end groups are preferably hydroxyl, ether, alkyl and acyl groups.

The use of plasticizers makes it possible to avoid extreme mixing ratios in many indications.

A further advantage of the use of plasticizers is the fact that, as already described above, solid starter components can be readily dissolved in the plasticizers.

DE 197 11 514 B4, which is likewise aimed at impression materials, additionally states that customary plasticizers are generally of good compatibility with polyether materials, and so the use thereof is advisable not just for economic reasons but also for improving the properties, especially for avoidance or reduction of possible crystallization processes. Suitable examples were said to be phthalic esters, glycol derivatives, polymeric plasticizers, sorbitan esters, etc. Customary plasticizers were said to be described, for example, in "Polyethers, part I", edited by Norman G. Gaylord, Interscience Publishers (1963). It is stated, however, that the addition of relatively large amounts of plasticizer to the impression materials can affect the water absorption, swelling and change in dimensions to such a degree that the impression becomes unusable.

DE 39 02 417 A1 discloses molding compositions for production of dental casting models. Here too, plasticizers are used. The publication refers to a "chemically inert" compound which is added to the compositions, "chemically inert" being understood to mean that the compound does not enter into any reactions with the organic polymerizable composition. The "chemically inert" compound thus does not have any functional groups reactive toward the polymerizable monomers, i.e. no double bonds such as polymerizable vinyl groups.

The publication specifies biphenyl, 1,2-diphenylethane, decanol, 2,4,6-trimethylnaphthalene, hexamethylbenzene, diphenylmethane, 1,1-diphenylethane, pentadecane, 2,3-dimethylbiphenyl, cinnamyl alcohol, dibenzyl ether, hexaethylbenzene and diethyl phthalate as suitable plasticizers.

DE 199 61 341 C2 is directed to temporary composite-based C&B materials, the aim being to improve fracture susceptibility with simultaneously high dimensional stability of these materials. The inventive compositions also comprise plasticizers in amounts of 1-40% by weight, preferably 2-30% by weight. The plasticizers should preferably have viscosities less than 10 Pas at 23° C. (cone-plate viscometer). Again polyethylene glycol derivatives, polypropylene glycols, low molecular weight polyesters, dibutyl phthalate, dioctyl phthalate, dinonyl phthalate, diphenyl phthalate, di(isononyl) adipate, tricresyl phosphate, paraffin oils and silicone oils are mentioned.

DE 197 54 029 A1 describes an elastic tooth restoration material and methods for producing tooth prosthetic material using the latter. In this application too, it is possible to use plasticizers. Preference is given to using phthalate plasticizers. Examples include phthalate derivatives, such as dimethyl phthalate, dibutyl phthalate and dioctyl phthalate.

DE 60 2004 009 552 T2 discloses an oral release system comprising an antibacterial agent and an inflammation inhibitor, which is suitable for the treatment of dental diseases, especially of periodontal diseases. In order to improve the flexibility of the system, a plasticizer or a mixture of plasticizers is added. It is said that type and amount of the plasticizer determines the flexibility of the composition. The following are mentioned as suitable plasticizers: phthalates such as dimethyl phthalate, dibutyl phthalate, diethyl phthalate, dibutyl sebacate, triethyl citrate, tributyl citrate, acetylated monoglycerides, acetyl tributyl citrate, triacetin, benzyl benzoate, glycol derivatives such as glycerol, polyethylene glycols, propylene glycol butyl, and/or glycol esters of fatty acids, refined mineral oils, oleic acid, castor oil, corn oil, camphor, and sugar alcohols such as sorbitol. Preferred plasticizers are sorbitol and glycerol, glycerol being the most preferred plasticizer. The preferred amount of plasticizer is in the range from 1 to 15% by weight and further preferably in the range from 4 to 10% by weight.

The patent claims a plasticizer selected from the group of glycol derivatives, phthalates, citrate derivatives, benzoates, butyl or glycol esters of fatty acids, highly refined mineral oils, camphor, oleic acid, castor oil, corn kernel oil and sugar alcohols.

DE 10 2008 283 306 A1 discloses a two-component, chemically curing, storage-stable dental composite material comprising nanodiamond. To establish particular properties, the inventive material may also comprise plasticizers.

The following are mentioned: polyethylene glycols, polypropylene glycols, unsaturated polyesters, phthalates, adipates, sebacates, phosphoric esters, phosphonic esters and/or citric esters.

DE 699 21 231 T2 describes a dental composition and a artificial tooth produced therefrom. This dental composition as well consists of a composite material, which means that it contains both an organic and an inorganic phase. The bond between the organic resin matrix and the inorganic filler surfaces is ensured with the aid of adhesion promoters. Examples of adhesion-promoting substances are organofunctional silanes, and titanate-based and zircoaluminate-based adhesion promoters. DE 699 21 231 T2 specifies several compounds for the various types of adhesion promoters. The amount of the adhesion promoter added to the dental composition is between 0.1 and 25 parts by weight per 100 parts by weight of the monomer. If the amount is more than 25 parts by weight, any excess of the adhesion promoter is said to act as a plasticizer.

DE 692 31 737 T2 relates to a root canal filling composition and to an adhesive composition. The heat-curable resin-based material of the inventive root canal composition also comprises a plasticizer in an amount between 0.1 and 30% by weight. The purpose of the plasticizer is to soften or to plasticize the resin, to such an extent that the material can readily be introduced into a root canal. The following are mentioned as suitable plasticizers: dibutoxyethoxyethyl adipate, dioctyl phthalate, dibutyl phthalate, butyl benzyl phthalate, alkyl benzyl phthalate, dialkyl adipate, 2-ethylhexyl diphenyl phosphate, isodecyl diphenyl phosphate, triphenyl phosphate and further esters.

The aim of DE 690 17 484 T2 is a chlorhexidine-containing composition for the treatment of periodontal or other diseases, wherein the chlorhexidine is to be released in a delayed manner. Again a plasticizer is used to regulate the flexibility of the final dried composition. The plasticizer must be provided in a sufficient amount to prevent the final composition from being too brittle. The plasticizer should be present in an amount of 0.01 to 15% by weight in the composition prior to drying. After the vaporization of 90% of the solvent, such compositions should contain 0.01 to 41% by weight of plasticizer. The following are named explicitly as plasticizers: phthalate esters, phosphate esters, glycol derivatives, hydrocarbons, oils or fatty acids, and glycerol and sorbitol have been found to be preferred plasticizers. The most preferred is glycerol.

DE 690 33 994 T2 also discloses liquid polymer compositions for prevention and treatment of dental or dermatological disorders. Again plasticizers are disclosed, for instance polyethylene glycol 400 to 4000, glycerol, sorbitol or mineral oil, which may be present in the compositions in concentrations of about 1% by weight.

DE 697 25 380 T2 describes liquid, light-curable compositions. According to the publication, such compositions are used to a wide extent as coating materials, as photoresists, as dental material or the like. For these compositions too, plasticizers are disclosed. Illustrative examples include dialkyl esters of phthalic acid, such as di-n-octyl phthalate, dimethyl phthalate, diethyl phthalate, dibutyl phthalate, diheptyl phthalate and di-2-ethylhexyl phthalate, triorgano esters of phosphoric acid such as tributyl phosphate, tri-2-ethylhexyl phosphate, triphenyl phosphate and tricresyl phosphate, dialkyl esters of adipic acid such as dibutyl adipate and di-n octyl adipate, and the like. The photocurable resin composition disclosed here may, in accordance with the invention, comprise one or a multitude of the plasticizers specified.

DE 698 01 010 T2 relates to a prosthetic restoration component with excellent biocompatibility, adequate hardness and mechanical strength, and methods for production thereof. Here the plasticizers disclosed for these systems are: phthalate esters (DOP, DEP, DBP), adipic esters, trimellitic esters and sebacic esters are mentioned.

DE 20 2010 014 676 U1 describes a duplicating composition which can also be used for production of negative impressions in the dental sector. According to the invention, this composition comprises 30 to 60% by weight of at least one polyhydric alcohol. The latter serves as a plasticizer and is supposed to contribute to the advantageous elastic properties of the negative impressions produced. The at least one polyhydric alcohol is preferably selected from the group comprising glycerol, sugar alcohols (e.g. sorbitol or mannitol), propylene glycol, polyethylene glycol and mixtures thereof, particular preference being given to the use of glycerol.

It is said to be particularly advantageous when the duplicating composition comprises 45 to 55% by weight of the at least one polyhydric alcohol, especially glycerol.

DE 199 41 738 B4 is aimed at polyurethane-based fillers for polymer formulations. As well as the inventive fillers, dental compositions formulated with the fillers may additionally comprise plasticizers to increase the flexibility of the compositions. Good suitability is said to be possessed, for example, by dibutyl, dioctyl and dinonyl phthalate, or dibutyl, dioctyl and dinonyl adipate, and also higher molecular weight polyphthalic esters and adipic esters.

DE 10 2009 046 251 A1 discloses a reactive one-component system. Such systems are of particular significance in the fields of sealants and adhesives. According to the publication, they can also be used in the medical sector, for example in the dental sector, in coatings such as lacquers or in reactive resins, for example road markings or industrial floors. The following are mentioned as plasticizers preferred for these one-component systems: esters, polyols, oils, low molecular weight polyethers or phthalates.

DE 2420351 C3 relates to the use of a composition as a root canal filling component. According to the publication, this dental composition requires an inert solvent (plasticizer) in order to dissolve the components and later to give rise to a polymer which can be removed again during a revision. Suitable compounds specified are water, glycerol and esters thereof, propylene glycol, 1,2-propanediol carbonate, pentaerythriol, diacetin, monoacetin, ethylene glycol, diethylene glycol and dipropylene glycol. However, within the examples of this patent diacetin (=glyceryl diacetate or 1,2,3-propanetriol 1,3-diacetate) is used exclusively.

For the use as plasticizers for the production of toxicologically favorable plastics the WO 00/78853 A1 specifies a whole series of cyclohexanepolycarboxylic acids and derivatives thereof. As well as the cyclohexanepolycarboxylic acids per se and derivatives thereof, especially mono-, di- or optionally tri- or tetraesters and anhydrides of the cyclohexanepolycarboxylic acids are proposed for use in plastics. The esters used are alkyl, cycloalkyl and alkoxyalkyl esters, where the alkyl, cycloalkyl and alkoxyalkyl groups may comprise generally 1 to 30, preferably 2 to 20 and more preferably 3 to 18 carbon atoms and wherein the alkyl residue can be linear or branched.

WO 00/78704 relates to selected cyclohexane-1,3- and -1,4-dicarboxylic esters, to the use thereof as plasticizers in plastics and to the preparation thereof by means of hydrogenation of the corresponding isophthalic and terephthalic esters by contacting one or more such isophthalic or terephthalic esters with a hydrogen-containing gas in the presence of a specific catalyst.

EP 1 042 273 B1 describes processes for hydrogenating benzenepolycarboxylic acids or derivatives thereof using a catalyst having macropores.

DE 28 23 165 specifies processes for preparing cycloaliphatic carboxylic esters.

The prior art regarding inert substances, or plasticizers in dental compositions or for production of toxicologically favorable plastics which, due to their low toxicity, would likewise be suitable as dental materials, thus describes a multitude of compounds.

With regard to use thereof in the dental sector, the plasticizers are utilized in one-component and multicomponent systems for a wide variety of different indications. They are used in free-radically crosslinkable systems, and likewise in drying or setting compositions. They are encountered in photocuring and chemically curing dental compositions. They are used in order to better (more exactly) blend multicomponent dental compositions and in order to optimize the properties of the resulting polymer. The plasticizing, flexibilizing effect of these inert compounds arises from the fact that the free, non-reactive chain ends of the plasticizers prevent a regular network structure. Their long chains distort and widen the structural framework. They may lie between the polymer chains and disrupt and prevent the formation of a majority of interactions between the individual molecular aggregates. Their mode of action is sometimes similar to that of a lubricant, which lies between the individual polymer layers and allows the polymers to slide past. The plasticizers are thus utilized as an elasticizing component in dental compositions which lowers the modulus of elasticity (and the glass transition temperature). In this context, it should be pointed out that the extent of the decrease in the mechanical strength of the materials in the case of use of many plasticizers from the prior art is disadvantageous.

In addition, plasticizers are also used in order to actively influence the reaction kinetics of a curable composition. For example, for temporary C&B materials, even in the case of systems with mixing ratios of 1:1, plasticizers are required since a sufficiently long elastic phase of the initially mixed composition is needed. It would be extremely difficult to achieve this without the use of plasticizers.

SUMMARY OF THE DISCLOSURE

The primary object of the present invention is to provide novel dental composite materials comprising one or more plasticizers. The plasticizers should have marked hydrophobic properties reflected, inter alia, in a very low water absorption and a very low water solubility of the inventive dental polymers obtainable using the plasticizers. In addition, the inventive dental materials obtainable using the plasticizers should feature good mechanical stability reflected, inter alia, in a high flexural strength. The use of the plasticizers should thus not exert any adverse effects on the mechanical values. By using the plasticizers it should preferably be possible to produce such inventive polymers which have low water absorption, low solubility and high flexural strength. In addition, the inventive composite materials should have reaction kinetics properties enabling advantageous processing times for the respective indications.

These objectives are achieved by a dental curable composite material comprising (a) one or more compound(s) of the structure $Q\text{-}[(Y)_n\text{---}X]_o$ which are not free-radically polymerizable during the curing with the constituents (b), where, here and hereinafter:

Q is a tricyclic structural element where one, two or more of the hydrogen atoms not substituted by $Y_n$—X substituents in this tricyclic structural element Q are optionally replaced by alkyl groups (preferably $C_1$-$C_4$-alkyl), alkoxy groups (preferably $C_1$-$C_4$-alkoxy), halogen atoms (preferably F) or trifluoromethyl groups;

Y is methylene (—$CH_2$—);

n=0 or 1;

X is —O—Z, —N—$(Z)_2$, —NH—Z, —O—C(=O)—Z, —C(=O)—O—Z, —O—C(=O)—NH—Z, —NH—C(=O)—O—Z, —NH—C(=O)—NH—Z, —C(=O)—NH—Z, —NH—C(=O)—Z, —C(=O)—N—$(Z)_2$, —N—(Z)—C(=O)—Z, —O—C(=O)—N(Z)—C(=O)—NH—Z, —NH—C(=O)—N(Z)—C(=O)—NH—Z, —N(C(=O)—NH—Z)$_2$, —C(=O)—N(Z)—C(=O)—NH—Z, —N(C(=O)—NH—Z)(C(=O)—Z), —N(C(=O)—NH—Z)(C(=O)—O—Z), wherein the bond arranged on the left in each formula is closer to the structural element Q and where X is selected such that Z has a minimum number of atoms, Z is an organic radical having at least one carbon atom, and different Z may be different, o=2, 3, 4, and (b) further constituents selected from the group consisting of (b-1) one or more different monomer(s), preferably selected from the group consisting of (meth)acrylates, (b-2) one or more fillers, (b-3) one or more photoinitiator(s) and/or one or more initiator(s) for chemical curing, (b-4) optionally one or more polymerization inhibitor(s), and (b-5) optionally one or more solvents.

DETAILED DESCRIPTION OF THE DISCLOSURE

Compounds which are not free-radically polymerizable with monomers are known to those skilled in the art. These compounds do not polymerize in the presence of initiator substances, for example peroxides, hydroperoxides, carboxylic peroxides or azo compounds, which decompose under the conditions of dental applications (standard pressure, ambient temperature or mouth temperature) and form free radicals. Further below standard initiator systems are mentioned, including photochemically active initiator systems. These compounds do not contain any activated ethylenically unsaturated bonds, such as (meth)acrylate functions, vinyl ether functions, allyl functions or double bonds, which are flanked by ester groups, as encountered in unsaturated polyesters. These also include vinyl and vinylidene groups in which the double bond is activated by halogen atoms, amine groups, thiol groups, ester groups, acid groups, cyano groups or aryl groups by direct substitution, and can thus react free-radically with monomers in the presence of initiators under the conditions of dental applications.

Of course these compounds do not react in chain-extending steps with carbon- or heteroatom-centered free radicals.

The inventive polymers obtainable by curing the inventive dental composites have marked hydrophobicity reflected, inter alia, in a very low water absorption and in a very low water solubility of the dental materials. In addition, the polymers obtainable by curing the inventive composite materials feature a high mechanical stability reflected, inter alia, in a high flexural strength of the dental materials. The inventive composite materials, especially according to the preferred configurations and embodiments, can be processed to give inventive polymers which have low water absorption, low solubility and high flexural strength. The tricyclic structural element Q of the plasticizing compound contributes to the high hydrophobicity which is reflected, inter alia, in a very low water absorption and very low water solubility of the polymers.

It has been found that the plasticizers of the $Q\text{-}[(Y)_n\text{---}X]_o$ structure have good processability to give the inventive composites. The curable composite compositions formulated incorporating the plasticizers can be produced in a simple manner. The cured polymers or materials are characterized by a low shrinkage, good adhesion on various substrates, high hydrolysis stability, low water absorption, low water solubility and high mechanical strength. The properties mentioned are extremely important within the field of dental technology.

Preference is given to using the plasticizers in inventive compositions which are free-radically crosslinkable. It has been observed that the plasticizers of the $Q\text{-}[(Y)_n\text{---}X]_o$ structure remain stable in the corresponding organic matrices of the inventive free-radically curable compositions. This includes both, the liquid or pasty uncured compositions and in the inventive crosslinked polymers, and the plasticizers do not exhibit any tendency to migrate. Possibly, the functional groups which bind to the polyalicyclic core of the plasticizers and have polar elements form a lasting and permanently overlying domain structure which accounts for the integrity of the plasticizer in the structural environment of the preferably free-radically curable compositions.

The term "tricyclic" corresponds to IUPAC nomenclature.

A plasticizer for an inventive dental composite material comprises at least one tricyclic structural element Q. In the context of the present invention, this means that o hydrogen atoms of the hydrocarbon are replaced by $Y_n$—X substituents, and optionally one, two or more of the hydrogen atoms unsubstituted by $Y_n$—X substituents are replaced by alkyl groups, alkoxy groups, halogen atoms or trifluoromethyl groups.

For unsubstituted tricycles, the following structures, for example, are possible:

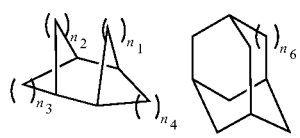

where $n_1$, $n_2$, $n_3$, $n_4$ and $n_6$ may each independently be a natural number from 0 to 5.

Examples include:

| | |
|---|---|
| when $n_1 = 2$; $n_2 = 0$; $n_3 = 2$; $n_4 = 3$ | tricyclo[4.3.2.0$^{2,5}$] undecane |
| when $n_1 = 0$; $n_2 = 1$; $n_3 = 2$; $n_4 = 3$ | tricyclo[5.2.1.0$^{2,6}$] decane |
| when $n_1 = 0$; $n_2 = 2$; $n_3 = 2$; $n_4 = 3$ | tricyclo[5.2.2.0$^{2,6}$] undecane |
| when $n_1 = 2$; $n_2 = 0$; $n_3 = 2$; $n_4 = 2$ | tricyclo[4.2.2.0$^{2,5}$] decane |
| when $n_6 = 1$ | tricyclo[3.3.1.1$^{3,7}$] decane |

Some di- or trisubstituted tricycles are shown by way of example below:

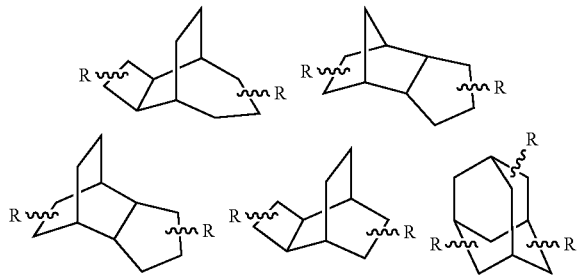

where R in each case denotes the other radicals of the compound.

Examples of tricyclic structural elements Q are the tricyclo[3.2.1.0$^{2,6}$]octane, the tricycle [4.2.1.0$^{2,6}$]-nonane, the tricyclo[5.2.1.0$^{2,6}$]decane, the tricyclo-[6.2.1.0$^{2,6}$]undecane, the tricyclo[7.2.1.0$^{2,6}$]dodecane, or the tricyclo[4.2.1.1$^{2,5}$]decane, the tricyclo-[4.3.1.1$^{2,5}$]decane, the tricyclo[4.4.1.1$^{2,5}$]decane, the tricyclo[2.2.1.0$^{2,6}$]heptane, the tricyclo[2.2.2.0$^{2,6}$]-octane, the tricyclo[3.2.2.0$^{2,6}$]nonane, the tricyclo-[3.3.1.1$^{3,7}$]decane, the tricyclo[3.2.1.1$^{3,7}$]nonane, the tricyclo[4.2.2.2$^{2,5}$]dodecane, the tricyclo[4.3.2.2$^{2,5}$]-tridecane, the tricyclo[4.4.2.2$^{2,5}$]tetradecane, the tricyclo[4.2.1.0$^{3,7}$]nonane, the tricyclo[4.4.1.1$^{1,5}$]dodecane, the tricyclo[6.2.1.0$^{2,7}$]undecane, the tricyclo[5.2.2.0$^{2,6}$]undecane, the tricyclo[6.2.2.0$^{2,7}$]dodecane, the tricyclo[4.3.2.0$^{2,5}$]undecane, the tricyclo[4.2.2.0$^{2,5}$]decane or the tricyclo[5.5.1.0$^{3,11}$]tridecane structural element.

In a preferred embodiment, the structure derives from a tricyclic [a.c.d.f]hydrocarbon. The sum of a, c, d and f is preferably in the range from 6 to 12, more preferably in the range from 7 to 9.

In a preferred embodiment, the structure derives from a tricyclic [a.2.1.0$^{2,(a+1)}$]hydrocarbon where a may in each case be the number 3, 4, 5, 6 or 7. In a further preferred embodiment, the structure derives from a tricyclic [a.2.2.0$^{2,(a+1)}$] hydrocarbon where a in each case may be the number 3, 4, 5, 6 or 7.

In a further preferred embodiment, the structure derives from a tricyclic [a.3.1.1]hydrocarbon where a in each case may be the number 3, 4, 5, 6 or 7.

In a preferred embodiment, an inventive dental composite material comprises one or more plasticizing compounds of the Q-[(Y)$_n$—X]$_o$ structure in which Z is selected from the group consisting of:

a.) hydrocarbyl radicals [—R$_1$] where the number of carbon atoms is 1 to 30, preferably 1 to 15 and more preferably 1 to 9, and where the radicals may be linear or branched, and b.) hydrocarbyl ether radicals [(—R$_2$—O)$_q$—R$_3$] where the number of carbon atoms for R$_2$ is 2 to 6, preferably 2 to 4 and more preferably 2 to 3, and where the number of carbon atoms for R$_3$ is 1 to 20, preferably 1 to 10 and more preferably 1 to 5, and where R$_2$ and R$_3$ may be linear or branched and where q=1 to 15, preferably 1 to 10 and more preferably 1 to 5, and c.) hydrocarbyl ester radicals [—R$_4$—(C=O)—O—R$_5$] and [—R$_4$—O—(C=O)—R$_5$] where the number of carbon atoms for R$_4$ and R$_5$ is 1 to 15, preferably 1 to 9 and more preferably 1 to 4, and where R$_4$ and R$_5$ may be linear or branched and d.) hydrocarbyl ester radicals [—R$_4$— ((C=O)—O—R$_5$)$_2$] and [—R$_4$—(O—(C=O)—R$_5$)$_2$] and e.) hydrocarbyl amino radicals [—R$_4$—N—(R$_5$)$_2$] and f.) alkoxylated hydrocarbyl ester radicals [(—R$_2$—O)$_q$—R$_4$— (C=O)—O—R$_5$] and [(—R$_2$—O)$_q$—R$_4$—O—(C=O)—R$_5$] and g.) substituted alkoxylated hydrocarbyl ester radicals [(—R$_2$—O)$_q$—CH$_2$—O—(C=O)—NH—R$_4$— (C=O)—R] and h.) hydrocarbyl alcohol radicals having a terminal hydroxyl group [—R$_4$—OH] and i.) hydrocarbyl alcohol radicals having one, two or more non-terminal/terminal hydroxyl group(s) and up to 30 carbon atoms and j.) alkoxylated hydrocarbyl alcohol radicals [(—R$_2$—O)$_q$—R$_4$—OH] and k.) ketone radicals [—R$_6$— (C=O)—R$_7$] where the number of carbon atoms for R$_6$ is 1 to 30, preferably 1 to 20 and more preferably 1 to 10, and where the number of carbon atoms for R$_7$ is 1 to 30, preferably 1 to 10 and very preferably 1, and where R$_6$ and R$_7$ may be linear or branched.

In a particularly preferred embodiment, an inventive dental composite material comprises one or more plasticizing compounds of the Q-[(Y)$_n$—X]$_o$ structure in which Z is selected from the group consisting of:

a.) hydrocarbyl radicals [—R$_1$] where the number of carbon atoms is 1 to 9 and where the radicals may be linear or branched and b.) hydrocarbyl ether radicals [(—R$_2$—O)$_q$—R$_3$] where the number of carbon atoms for R$_2$ is 2 to 3 and where the number of carbon atoms for R$_3$ is 1 to 5 and where R$_2$ and R$_3$ may be linear or branched and where q=1 to 5 and c.) hydrocarbyl ester radicals [—R$_4$— (C=O)—O—R$_5$] and [—R$_4$—O—(C=O)—R$_5$] where the number of carbon atoms for R$_4$ and R$_5$ is 1 to 4 and where R$_4$ and R$_5$ may be linear or branched and d.) hydrocarbyl ester radicals [—R$_4$— ((C=O)—O—R$_5$)$_2$] and [—R$_4$— (O—(C=O)—R$_5$)$_2$] and e.) hydrocarbyl amino radicals [—R$_4$—N—(R$_5$)$_2$] and f.) alkoxylated hydrocarbyl ester radicals [(—R$_2$—O)$_q$—R$_4$— (C=O)—O—R$_5$] and [(—R$_2$—O)$_q$—R$_4$—O—(C=O)—R$_5$] and g.) substituted alkoxylated hydrocarbyl ester radicals [(—R$_2$—O)$_q$—CH$_2$—O—(C=O)—NH—R$_4$— (C=O)—R] and h.) hydrocarbyl alcohol radicals [—R$_4$—OH] and i.) hydrocarbyl alcohol radicals having one, two or more non-terminal/terminal hydroxyl group(s) and up to 30 carbon atoms and j.) alkoxylated hydrocarbyl alcohol radicals [(—R$_2$—O)$_q$—R$_4$—OH] and k.) ketone radicals [—R$_6$—(C=O)—R$_7$] where the number of carbon atoms for R$_6$ is 1 to 10, and where the number of carbon atoms for R$_7$ is 1 and where R$_6$ may be linear or branched.

A preferred inventive composite material is a dental composition that is curable chemically and/or by light induction and/or thermal induction.

A particularly preferred inventive dental composite material is composed of the following constituents:

Constituent (a)—Plasticizer

Constituent (a) is preferably selected from the group consisting of 3(4),8(9)-bis(acyloxymethyl)tricyclo [5.2.1.0$^{2,6}$] decane, alkoxylated 3(4),8(9)-bis(acyloxy-methyl)tricyclo [5.2.1.0$^{2,6}$]decane, 1,3,5-triacyloxy-tricyclo[3.3.1.1$^{3,7}$] decane, alkoxylated triacyloxytricyclo[3.3.1.1$^{3,7}$]decane, tricyclo-[5.2.1.0$^{2,6}$]decane-3(4),8(9)-dicarboxylic ester, the Michael-type adduct of 3(4),8(9)-bis(aminomethyl)-tricyclo [5.2.1.0$^{2,6}$]decane and acrylic ester, 3(4),8(9)-bis(alkyloxymethyl)tricyclo[5.2.1.0$^{2,6}$]decane, alkoxylated 3(4),8 (9)-bis(alkyloxymethyl)tricyclo-[5.2.1.0$^{2,6}$]decane, the addition product of 3(4),8(9)-bis(hydroxymethyl)tricycle [5.2.1.0$^{2,6}$]decane with isocyanate, the addition product of alkoxylated 3(4),8(9)-bis(hydroxymethyl)tricyclo[5.2.1.0$^{2,6}$]decane with isocyanate, the addition product of 3(4),8 (9)-bis(aminomethyl)tricyclo[5.2.1.0$^{2,6}$]decane with isocyanate or the reaction product of 3(4),8(9)-bis(isocyanatomethyl)tricycle [5.2.1.0$^{2,6}$]decane with amines, the addition product of alkoxylated 3(4),8(9)-bis(aminomethyl)tricyclo [5.2.1.0$^{2,6}$]decane with isocyanate, the addition product of 3(4),8(9) bis(isocyanatomethyl)tricyclo[5.2.1.0$^{2,6}$]decane with alcohol, the addition product of 3(4),8(9) bis(isocyanatomethyl)tricyclo[5.2.1.0$^{2,6}$]decane with alkoxylated alcohol, the reaction product of 3(4),8(9) bis(carbonyl halide) tricyclo[5.2.1.0$^{2,6}$]decane with an amine, or the reaction product of 3(4),8(9)-bis(carboxylic acid)tricyclo[5.2.1.0$^{2,6}$] decane with an isocyanate, the reaction product of 3(4),8(9) bis(isocyanatomethyl)tricyclo[5.2.1.0$^{2,6}$]decane with an amino alcohol, the reaction product of 3(4),8(9) bis(isocyanatomethyl)tricyclo[5.2.1.0$^{2,6}$]decane with an amino alcohol and subsequent alkoxylation of the resulting alcohol, the reaction product of 3(4),8(9) bis(isocyanatomethyl)tricyclo [5.2.1.0$^{2,6}$]decane with an amino alcohol, subsequent alkoxylation of the resulting alcohol and reaction of this compound with carboxylic acid/carboxylic anhydride, the reaction product of 3(4),8(9)-bis(aminomethyl)tricyclo[5.2.1.0$^{2,6}$]decane with alkyl halides, the reaction product of 3(4),8(9) bis(aminomethyl)tricyclo[5.2.1.0$^{2,6}$]decane with acid halides, or the reaction product of 3(4),8(9) bis(isocyanatomethyl)tricyclo [5.2.1.0$^{2,6}$]decane with carboxylic acids, the reaction product of 3(4),8(9)-bis(hydroxymethyl)tricyclo[5.2.1.0$^{2,6}$]decane, or of alkoxylated 3(4),8(9)-bis(hydroxymethyl)tricyclo-[5.2.1.0$^{2,6}$]decane, with fatty acids and the further reactions thereof, in the case of reaction products of unsaturated fatty acids, to give the corresponding ketones by the Wacker process, the reaction product of 3(4),8(9)-bis(aminomethyl)tricyclo[5.2.1.0$^{2,6}$]decane with epoxides and the further reaction product thereof with carboxylic acids, alkoxylated 3(4),8(9)-bis(hydroxymethyl)tricyclo[5.2.1.0$^{2,6}$]decane and alkoxylated 3(4),8(9)-bis(aminomethyl)tricyclo-[5.2.1.0$^{2,6}$] decane.

Constituent (b-1) Polymerizable monomers

The polymerizable monomers are preferably free-radically polymerizable monomers, which are preferably substances having one, two or more ethylenic groups, for example but not limited to the (meth)acrylate monomers used customarily in dental chemistry.

The (meth)acrylate monomers may be monofunctional and polyfunctional. Monofunctional (meth)acrylate monomers used with preference are the esters of (meth)acrylic acid having alkyl groups of 1 to 12 carbon atoms, and esters of (meth)acrylic acid containing aromatic groups having 6 to 12 carbon atoms, where the alkyl groups and aromatic groups which form the esters may contain substituents such as hydroxyl groups and ether bonds.

The patent literature specifies a multitude of further compounds (for example including DE 39 41 629 A1, which is part of the present application by way of reference), all of which are esters of acrylic or methacrylic acid and are suitable for use in an inventive curable dental composite material.

The free-radically polymerizable monomers may also be hydroxyl compounds having at least one ethylenic double bond. It is preferred to use the hydroxyl compounds of (meth) acrylates used customarily in dental chemistry.

Other examples of polyfunctional (meth)acrylate monomers include di(meth)acrylates of alkylene glycol having 2 to 20 carbon atoms, di(meth)acrylates of oligomers of alkylene glycol, polyalkylene glycol di(meth)acrylate, di(meth)acrylates of bisphenol A or of the diglycidyl ether of bisphenol A.

Particular preference is further given to free-radically curable compounds based on a central polyalicyclic structural element, for example 3(4),8(9)-bis((meth)acryloyloxymethyl)tricyclo-[5.2.1.0$^{2,6}$]decane, alkoxylated 3(4),8(9)-bis ((meth)acryloyloxymethyl)tricyclo[5.2.1.0$^{2,6}$]decane, 2,3-bis((meth)acryloyloxymethyl)bicyclo [2.2.1]heptane, alkoxylated 2,3-bis((meth)acryloyloxymethyl)bicyclo-[2.2.1]heptane, 1,3,5-tri(meth)acryloyloxytricyclo-[3.3.1.1$^{3,7}$]decane, alkoxylated tri(meth)acryloyl-oxytricyclo [3.3.1.1$^{3,7}$]decane and (meth)acrylic esters of tricyclo [5.2.1.0$^{2,6}$]decane-3(4),8(9)-dimethanol, alkoxylated tricyclo[5.2.1.0$^{2,6}$]decane-3 (4),8(9)-dimethanol, bicyclo[2.2.1] heptane-2,3-dimethanol, alkoxylated bicyclo[2.2.1]heptane-2,3-dimethanol, 1,3,5-adamantanetriol, alkoxylated 1,3,5-adamantanetriol, with arrangement of urethane, urea, amide, allophanate, acylurea or biuret groups between the polyalicyclic structural element and the (meth)acrylic esters.

Details of the preparation of these substituted (meth) acrylic esters can be found in the as yet unpublished patent applications EP 11 183 333, EP 11 183 328, EP 11 183 345, EP 11 183 338, EP 11 183 342 and EP 11 188 086, and in the literature cited in these documents. These references are likewise part of the present application by way of reference.

Preference is likewise given to urethane (meth)acrylates, reaction products of 2 mol of a (meth)acrylate having a hydroxyl group and 1 mol of a diisocyanate.

In addition, it is also possible to use free-radically curable monomers having ethylenic double bonds based on polysiloxanes, as described, for example, in DE 199 03 177 or in DE 44 16 857, which are part of the present application by way of reference.

In a preferred inventive curable dental composite material, constituent (b-1) comprises one or more (meth)acrylate monomers selected from the group consisting of 3(4),8(9)-bis((meth)acryloyloxymethyl)-tricyclo[5.2.1.0$^{2,6}$]decane, alkoxylated 3(4),8(9)-bis((meth)acryloyloxymethyl)tricyclo [5.2.1.0$^{2,6}$]decane, 2,3-bis((meth)acryloyloxymethyl)bicyclo [2.2.1]heptane, alkoxylated 2,3-bis((meth)acryloyloxymethyl)bicyclo[2.2.1]heptane, 1,3,5-tri(meth) acryloyloxytricyclo[3.3.1.1$^{3,7}$]decane, alkoxylated tri(meth) acrylyol-oxytricyclo[3.3.1.1$^{3,7}$]decane (meth)acrylic esters of tricyclo[5.2.1.0$^{2,6}$]decane-3(4),8(9)-dimethanol, alkoxylated tricyclo[5.2.1.0$^{2,6}$]decane-3 (4),8(9) dimethanol, bicyclo[2.2.1]heptane-2,3-dimethanol, alkoxylated bicyclo [2.2.1]heptane-2,3-dimethanol, 1,3,5-adamantanetriol, alkoxylated 1,3,5-adamantanetriol, with arrangement of urethane, urea, amide, allophanate, acylurea or biuret groups between the polyalicyclic structural element and the (meth) acrylic esters, ethylene glycol di(meth)acrylate, 1,6-hexanediol di(meth)acrylate (HEDMA), triethylene glycol di(meth)acrylate (TEDMA), 1,12-dodecanediol di(meth) acrylate, bisphenol A di(meth)acrylate, alkoxylated bisphenol A di(meth)acrylate, bisphenol B di(meth)acrylate, alkoxylated bisphenol B di(meth)acrylate, bisphenol C di(meth)acrylate, alkoxylated bisphenol C di(meth)acrylate, bisphenol F di(meth)acrylate, alkoxylated bisphenol F di(meth)acrylate, polyethylene glycol di(meth)acrylate, 7,7,9-trimethyl-4,13-dioxo-5,12-diazahexadecane 1,16-dioxydi (meth)acrylate (UDMA), butanediol di(meth)acrylate, tetraethylene glycol di(meth)-acrylate, neopentyl glycol di(meth) acrylate, 2-hydroxypropyl 1,3-di(meth)acrylate, 3-hydroxypropyl 1,2-di(meth)acrylate, pentaerythritol di(meth)acrylate, di(meth)acrylates of dihydroxymethyltricyclo[5.2.1.0$^{2,6}$]decane, 2-hydroxyethyl (meth)acrylate, 2-hydroxypropyl (meth)acrylate, 3-hydroxypropyl (meth)acrylate, 1,2-dihydroxypropyl (meth)acrylate, 1,3-dihydroxypropyl (meth)acrylate, 2,2-bis[4-[3-(meth) acryloyloxy-2-hydroxypropoxy]phenyl]propane (bis-GMA), trimethylolpropane tri(meth)acrylate, trimethylolethane tri(meth)acrylate, pentaerythritol tri(meth)acrylate, trimethylolmethane tri(meth)acrylate, pentaerythritol tetra(meth)acrylate, ditrimethylolpropane tetra(meth)acrylate, pentaerythritol hexa(meth)acrylate, butylene glycol di(meth)acrylate, propylene glycol di(meth)-acrylate, nonanediol di(meth)acrylate, decanediol di(meth)acrylate, glyceryl mono(meth)acrylate, glyceryl di(meth)acrylate, trimethylolpropane mono(meth)-acrylate, trimethylolpropane di(meth)acrylate, sorbitol mono-, di-, tri-, tetra- or penta(meth)acrylate, methyl (meth)acrylate, ethyl (meth)acrylate, propyl (meth)-acrylate, butyl (meth)acrylate, hexyl (meth)acrylate, tetrahydrofurfuryl (meth)acrylate, lauryl (meth)acrylate, cyclohexyl (meth)acrylate, allyl (meth)-acrylate, glycidyl (meth)acrylate, 2-ethoxyethyl (meth)acrylate, methoxy polyethylene glycol (meth) acrylate, isobornyl (meth)acrylate, 2-(N,N-dimethyl amino)ethyl (meth)acrylate, N-methylol (meth)acrylamide, diacetone(meth)acrylamide, 2,2-bis[4-(meth)acryloyloxyphenyl]propane, 2,2-bis[4-(meth)acryloyloxyethoxyphenyl]propane, 2,2-bis[4-(meth)acryloyloxydiethoxyphenyl]propane, 2,2-bis[4-(meth)acryloyloxytriethoxyphenyl]propane, 2,2-bis[4-(meth)acryloyloxytetraethoxyphenyl]propane, 2,2-bis[4-(meth)acryloyloxypentaethoxyphenyl]propane, 2,2-bis[4-(meth)acryloyloxydipropoxyphenyl]propane, 2,2-bis[4-(meth)acryloyloxyethoxyphenyl]-2-[4-(meth)acryloyloxydiethoxyphenyl]-propane, 2-[4-(meth)acryloyloxydiethoxyphenyl]-2-[4-(meth)acryloyloxytriethoxyphenyl]propane, 2-[4-(meth)-acryloyloxdipropoxyphenyl]-2-[4-(meth)acryloyloxytriethoxyphenyl]propane, 2,2-bis[4-(meth)acryloyloxyisopropoxyphenyl]propane, hydroxypivalic acid neopentyl glycol di(meth)acrylate, acetoacetoxyethyl (meth)acrylate, polypropylene glycol di(meth)acrylate, glyceryl alkoxylate dimethacrylate, neopentyl glycol (meth)acrylate, N,N-(1,2-dihydroxyethylene)bis-acrylamide, 2,2-bis[4-(meth)acryloyloxypentaethoxy-phenyl]propane, 2,2-bis[4-(meth)acryloyloxypolyethoxy-phenyl]propane, diethylene glycol di(meth)acrylate, dipentaerythritol tetra(meth)acrylate, dipentaerythritol hexa(meth)acrylate, N,N-(2,2,4-trimethylhexamethylene)bis[2-(aminocarboxy)propane-1,3-diol]tetra (meth)acrylate, the condensation product of 3,(4)-(meth)acryloxymethyl-8,(9)-hydroxymethyltricyclo[5.2.1.0$^{2,6}$]decane with dicarboxylic acids, 2-ethylhexyl (meth)acrylate, tridecyl (meth)acrylate, stearyl (meth)acrylate, cyclohexyl (meth)acrylate, benzyl (meth)acrylate, methoxy diethylene glycol (meth)acrylate, dicyclopentenyl (meth)acrylate, phenyl (meth)acrylate, pentaerythritol mono(meth)acrylate, dipentaerythritol mono(meth)acrylate, caprolactone modified tetrahydrofurfuryl (meth)acrylate, and light curable monomers based on polysiloxanes.

Constituent (b-2)—Fillers

As constituent (b-2) organic and/or inorganic fillers may be used.

Inorganic fillers can be used alone or as mixtures. To optimize the product properties, the inorganic fillers can be introduced into the formulations in different particle sizes. The fillers may have a unimodal or polymodal, for example a bimodal, distribution.

The mean particle size $d_{50}$ of the filler particles to be used in accordance with the invention for the filler component (b-2) of an inventive mixture is determined by means of light scattering (laser diffraction), preferably with a Beckman Coulter LS13320 particle size measuring instrument.

The inorganic fillers used are compact glasses and different silicas in various sizes and states (monodisperse, polydisperse).

Suitable inorganic constituents are, for example, amorphous materials based on mixed oxides of $SiO_2$, $ZrO_2$ and/or $TiO_2$, microfine fillers such as fumed silica or precipitated silica, and macro- or mini-fillers such as quartz glass ceramic or glass powder, barium silicate glasses, barium fluorosilicate glasses, strontium silicate glasses, strontium borosilicate, Li/Al silicate glasses, barium glasses, calcium silicates, sodium aluminum silicates, fluoroaluminum silicate glasses, oxides of aluminum or silicon, zeolites, apatite, zirconium silicates, sparingly soluble metal salts such as barium sulfate or calcium fluoride, and X-ray-opaque fillers such as ytterbium fluoride.

For better incorporation into the polymer matrix, the fillers may be surface-modified. Examples include the surface treatment of the fillers with a silane. A particularly suitable adhesion promoter is methacryloyloxypropyltrimethoxysilane.

To adjust the rheological properties, inventive curable mixtures and products may comprise different silicas, preferably fumed silicas.

In addition, it is possible to use reinforcing materials such as glass fibers, polyamide fibers or carbon fibers. The inventive curable mixtures and products may additionally comprise fine splinters or bead polymers, where the bead polymers may be homo- or copolymers of organic curable monomers.

The inventive curable mixtures and products, especially for use in the dental sector, preferably comprise nanoscale solid particles. The nanoscale solid particles are particles having a mean particle size of not more than 200 nm, preferably not more than 100 nm and especially not more than 70 nm. The nanoscale inorganic solid particles are preferably those of oxides, sulfides, selenides and tellurides of metals, semimetals and mixtures thereof. Particular preference is given to nanoscale particles of $SiO_2$, $TiO_2$, $ZrO_2$, ZnO, $SnO_2$ and $Al_2O_3$ and mixtures thereof. The nanoscale solid particles are produced in a known manner, for example by flame pyrolysis, plasma processes, gas phase condensation, colloidal techniques, precipitation processes, sol-gel processes, etc. Preference is given to nanoscale inorganic solid particles with organic surface modification.

In a preferred configuration, the nanoscale particles are in nonagglomerated and/or nonaggregated form, for example dispersed in a medium, preferably in monodisperse form.

In order to achieve good incorporation of the nanoparticles into the polymer matrix of an inventive curable mixture or product, the surfaces of the nanoparticles (preferably of the preferred oxidic nanoparticles) have organic modification, i.e. the surfaces thereof have organic structural elements. Examples include the surface treatment of the fillers with a silane, which forms silanized nanoparticles. A particularly suitable adhesion promoter is methacryloyloxypropyltrimethoxysilane.

In a further preferred configuration, the nanoscale particles are nonagglomerated and/or nonaggregated, organically surface-modified nanoparticles having a mean particle size of less than 200 nm, preferably less than 100 nm, more preferably less than 70 nm, which have in turn preferably been silanized.

Constituent (b-3)—Photoinitiators

Examples of a light curing initiator include catalysts which only have photosensitizing action, and combinations of sensitizer and accelerator.

Examples of photosensitizers are alpha-diketones, benzoin alkyl ethers, thioxanthones, benzophenones, acylphosphine oxides, acetophenones, ketals, titanocenes, sensitizing dyes, etc. The sensitizers can be employed alone or in combination. Specific substance examples from the different classes can be found, for example, in DE 10 2006 019 092 A1 or in DE 39 41 629 C2, which are part of the present application by way of reference.

Examples of accelerators which are used together with the sensitizers are tertiary amines, secondary amines, barbituric acids, tin compounds, aldehydes and sulfur compounds. Specific substance examples of the different classes can be found in DE 10 2006 019 092 or in DE 39 41 629 C2, which are part of the present application by way of reference.

Further suitable initiators and initiator combinations are described in DE 601 16 142, which are part of the present application by way of reference.

The photoinitiators usable in the context of the present invention are characterized in that they can initiate the curing of an inventive curable mixture by absorption of light in the wavelength range from 300 nm to 700 nm, preferably from 350 nm to 600 nm and more preferably from 380 nm to 500 nm, optionally in combination with one or more coinitiators.

The absorption maximum of camphorquinone (CQ) is at approx. 470 nm and is thus within the blue light region. Camphorquinone (CQ) is one of the PI2 initiators and is regularly used together with a coinitiator.

An inventive curable mixture preferably comprises the combination of an alpha-diketone and an aromatic tertiary amine, preference being given to the combination of camphorquinone (CQ) and ethyl p-N,N-dimethylaminobenzoate (DABE).

Preference is likewise given to the further combination of the "alpha-diketone/aromatic tertiary amine" system with a phosphine oxide, especially with phenylbis(2,4,6-trimethylbenzoyl)phosphine oxide and/or 2,4,6-trimethylbenzoyl-diphenylphosphine oxide. With regard to the structures of suitable phosphine oxides for use in inventive curable mixtures, reference is made to publications DE 38 01 511 C2, DE 10 2006 050 153 A1, EP 0 184 095 B1, DE 42 31 579 C2, EP 0 366 977 B1, U.S. Pat. No. 7,081,485 B2, DE 32 36 026 A1, US 2007/0027229 A1, EP 0 262 629 B1, EP 0 073 413, U.S. Pat. No. 7,148,382 B2, U.S. Pat. No. 5,761,169, DE 197 08 294 A1, EP 0 057 474, EP 0 047 902 A, EP 0 007 508, DE 600 29 481 T2, EP 0 980 682 B1, EP 0 948 955 B1, EP 1 236 459 B1 and EP 0 173 567 A2, which are part of the present application by way of reference.

The phosphine oxides specified in these publications are particularly suitable, alone or in combination with the "alpha-diketone/amine" system, as a photopolymerization initiator system in the inventive mixtures.

Alternatively, it is also possible to use borate salts as described, for example, in U.S. Pat. Nos. 4,772,530, 4,954,414, 4,874,450, 5,055,372 and 5,057,393 as photoinitiators, which are part of the present application by way of reference.

Further suitable photoinitiators are described in J.-P. Fouassier, Photoinitiation, Photopolymerization and Photocuring, Hanser Publishers, Munich, Vienna, N.Y. 1995 and in J. F. Rabek (Ed.), Radiation Curing in Polymer Science and Technology, Vol. II, Elsevier Applied Science, London, N.Y. 1993, which are part of the present application by way of reference.

Constituent (b-3)—Initiators for Chemical Curing

The person skilled in the art is aware of various initiators for chemical curing. In this regard, EP 1 720 506 is a part of this application by way of reference.

Preferred initiators for chemical curing are benzoyl peroxide, lauroyl peroxide, especially dibenzoyl peroxide in combination with amines such as N,N-dimethyl-p-toluidine, N,N-dihydroxyethyl-p-toluidine, and structurally related amines.

The peroxides and the amines are divided between two different components of the dental material. When the amine-containing component (called base paste) is mixed with the peroxide-containing component (called initiator or catalyst paste), the reaction of amine and peroxide (redox reaction) initiates the free-radical reaction.

Dual-curing systems comprise a combination of photoinitiators and initiators for chemical curing.

For example, the base paste may additionally comprise a photoinitiator, such that the base paste can be used either alone as a light-curing dental material or together with the initiator paste as a light- and self-curing dental material.

As well as the oxidative organic peroxide compounds, the redox systems used may also be represented by barbituric acids or barbituric acid derivatives and malonylsulfamides.

Among the barbituric acid systems, the "Bredereck systems" are of high significance. Examples of suitable Bredereck systems and references to the corresponding patent literature can be found in EP 1 839 640, and also in DE 1495520, WO 02/092021 or WO 02/092023, which are part of the present application by way of reference.

Suitable malonylsulfamides are described in EP 0 059 451, which is part of the present application by way of reference. Preferred compounds are 2,6-dimethyl-4-isobutylmalonylsulfamide, 2,6-diisobutyl-4-propylmalonylsulfamide, 2,6-dibutyl-4-propylmalonyl-sulfamide, 2,6-dimethyl-4-ethyl-malonylsulfamide and 2,6-dioctyl-4-isobutylmalonylsulfamide.

In addition, it is possible to use sulfur compounds in the +2 or +4 oxidation state, such as sodium benzenesulfinate or sodium para-toluenesulfinate.

To accelerate the curing, the polymerization can be performed in the presence of heavy metal compounds such as Ce, Fe, Cu, Mn, Co, Sn or Zn, particular preference being given to copper compounds. The heavy metal compounds are preferably used in the form of soluble organic compounds. Preferred copper compounds are copper benzoate, copper acetate, copper ethylhexanoate, copper di(methacrylate), copper acetylacetonate and copper naphthenate.

Constituent (b-4)—Polymerization Inhibitors

The inventive curable dental composite materials preferably comprise one or more inhibitors, also called stabilizers. These are added to a curable mixture in order to avoid spontaneous polymerization. They react with prematurely formed free radicals, which are captured, prevent premature polymerization and increase the storage stability of the curable dental composite material. Standard inhibitors are phenol derivatives such as hydroquinone monomethyl ether (HQME) or 2,6-di-tert-butyl-4-methylphenol (BHT). Further inhibitors, such as 2,2-diphenyl-1-picrylhydrazyl, galvinoxyl and triphenylmethyl radicals, 2,3,6,6-tetramethyl-piperidinyl-1-oxyl radicals (TEMPO) and derivatives of TEMPO, or phenothiazine and derivatives of this compound, are described in EP 0 783 880 B1, which is part of the present application by way of reference. Alternative inhibitors are specified in DE 101 19 831 A1 or in EP 1 563 821 A1, which are part of the present application by way of reference.

Constituent (b-5)—Solvent

Suitable solvents are those used customarily, for example hydrocarbons, ketones and esters, for example toluene, xylene, isooctane, acetone, butanone, methyl isobutyl ketone, ethyl acetate, butyl acetate, tetrahydrofuran, N-methylpyrrolidone, dimethylacetamide and dimethylformamide. It is also possible to use alcohols such as ethanol, propanols, butanols, pentanols, hexanols, cyclohexanol, heptanols, octanols, nonanols, decanols, etc. Likewise suitable are cycloaliphatic or arylaliphatic alcohols.

It is especially preferable that the stoichiometry of the reactions, in the synthesis of plasticizer (a), of 3(4),8(9)-bis(hydroxymethyl)tricyclo[5.2.1.0$^{2,6}$]decane with isocyanate or of alkoxylated 3(4),8(9)-bis(hydroxymethyl)tricyclo[5.2.1.0$^{2,6}$]decane with isocyanate ranges from 1:1 to 1:2, such that the reaction products may comprise urethanes, allophanates and mixtures thereof in which the urethanes have not reacted fully to give the allophanates, 3(4),8(9)-bis(aminomethyl)tricyclo[5.2.1.0$^{2,6}$]decane with isocyanate or of alkoxylated 3(4),8(9)-bis(aminomethyl)tricyclo[5.2.1.0$^{2,6}$]decane with isocyanate ranges from 1:1 to 1:2, such that the reaction products may comprise ureas, biurets and mixtures thereof in which the ureas have not reacted fully to give the biurets, 3(4),8(9)-bis(carboxylic acid)tricyclo[5.2.1.0$^{2,6}$]decane with isocyanate ranges from 1:1 to 1:2, such that the reaction products may comprise amides, acylureas and mixtures thereof in which the amides have not reacted fully to give the acylureas, 3(4),8(9)-bis(carbonyl halide)tricyclo[5.2.1.0$^{2,6}$]decane with amine is 1:1 and gives an amide, and the second reaction stage to give the acylurea with a monoisocyanate is effected in a stoichiometry up to 1:1, such that the reaction product may comprise amides, acylureas and mixtures thereof, 3(4),8(9)-bis(isocyanatomethyl)tricyclo[5.2.1.0$^{2,6}$]decane with alcohol or with alkoxylated alcohol is 1:1 and gives a urethane, and the second reaction stage to give the allophanate with a monoisocyanate is effected in a stoichiometry up to 1:1, such that the reaction product may comprise urethanes, allophanates and mixtures thereof, 3(4),8(9)-bis(isocyanatomethyl)tricyclo[5.2.1.0$^{2,6}$]decane with amine is 1:1 and gives a urea, and the second reaction stage to give the biuret with a monoisocyanate is effected in a stoichiometry up to 1:1, such that the reaction product may comprise ureas, biurets and mixtures thereof, 3(4),8(9)-bis(isocyanatomethyl)tricyclo[5.2.1.0$^{2,6}$]decane with carboxylic acid is 1:1 and gives an amide, and the second reaction stage to give the acylurea with a monoisocyanate is effected in a stoichiometry up to 1:1, such that the reaction product may comprise amides, acylureas and mixtures thereof, 3(4),8(9)-bis(aminomethyl)tricyclo[5.2.1.0$^{2,6}$]decane with acid halides is 1:1 and gives an amide, and the second reaction stage to give the acylurea with a monoisocyanate is effected in a stoichiometry up to 1:1, such that the reaction product may comprise amides, acylureas and mixtures thereof.

The amounts of components present in preferred inventive composite materials are as follows:
(a) 0.5 to 20% by weight, preferably 2 to 10% by weight
(b-1) 5 to 90% by weight, preferably 25 to 80% by weight
(b-2) 1 to 85% by weight, preferably 20 to 75% by weight
(b-3) 0.05 to 8% by weight, preferably 0.5 to 4% by weight
(b-4) 0 to 1% by weight, preferably 0.01 to 0.2% by weight
(b-5) 0 to 85% by weight, preferably 0 to 75% by weight.

The amounts of components present in particularly preferred inventive composite materials are as follows:
(a) 2 to 10% by weight
(b-1) 25 to 80% by weight
(b-2) 20 to 75% by weight
(b-3) 0.5 to 4% by weight
(b-4) 0.01 to 0.2% by weight
(b-5) 0 to 75% by weight.

A particularly preferred inventive dental material comprises
(a) 2 to 10% by weight of a plasticizer selected from the group consisting of 3(4),8(9)-bis(acetyl-oxymethyl)tricyclo [5.2.1.0$^{2,6}$]decane, alkoxylated 3(4),8(9)-bis(acetyloxymethyl)tricyclo-[5.2.1.0$^{2,6}$]decane, 1,3,5-triacetyloxytricyclo-[3.3.1.1$^{3,7}$]decane, alkoxylated triacetyl oxytricyclo[3.3.1.1$^{3,7}$]decane, tricyclo-[5.2.1.0$^{2,6}$]decane-3(4),8(9)-dicarboxylic acid ethyl ester and the Michael-type adduct of 3(4), 8(9)-bis(aminomethyl)tricyclo[5.2.1.0$^{2,6}$]decane and methyl acrylate,
(b-1) 25 to 80% by weight of a free-radically curable monomer selected from the group consisting of 7,7,9-trimethyl-4,13-dioxo-5,12-diazahexadecane-1,16-dioxy di(meth)acrylate (UDMA), triethylene glycol di(meth)acrylate (TEDMA) and 3(4),8(9)-bis(methacryloyloxymethyl) tricyclo[5.2.1.0$^{2,6}$]decane,
(b-2) 20 to 75% by weight of a filler selected from the group consisting of glass ceramic, silicas, X-ray-opaque fillers, nanoscale fillers below 200 nm, the latter preferably being non agglomerated and/or non-aggregated, and organic polymers,
(b-3) 0.5 to 4% by weight of a photoinitiator selected from the group consisting of camphorquinone/amine and phosphine oxide and/or a chemical initiator selected from the group consisting of peroxide/amine and barbituric acid/barbituric acid derivatives in combination with heavy metal salts.

A particularly preferred inventive curable dental composite material is a two-component system, in which constituent (b-3) comprises a redox system comprising a reducing agent and an oxidizing agent, and the dental composite material being in the form of two spatially separate components in the form of pastes, and the reducing agent being present in the first component and the oxidizing agent in the second component, and constituents (a), (b-1), (b-2), optionally (b-4) and optionally (b-5) being present in the first and/or second component, and the pastes being present in mixing ratios of first component to second component in the ratio of 10:1 to 1:10.

Likewise in accordance with the invention is a dental material obtainable by curing an inventive dental composite material.

Also in accordance with the invention is a process for producing a dental material, comprising the steps of:
a.) providing one or more compounds (a) and (b),
b.) producing a mixture by mixing the compounds (a) and (b) provided,
c.) curing the constituents, the curing being induced either chemically and/or with light induction and/or with thermal induction.

Hereinafter, the invention is illustrated in detail for compounds comprising tricyclic structural elements Q using the example of tricyclo[5.2.1.0$^{2,6}$]decane (TCD) derivatives. The reactions can likewise also be performed with other tricyclic compounds.

The inventive plasticizers are synthesized by the conventional organic chemistry methods.

I. Synthesis of the Plasticizers Proceeding from the Alcohol

Bis(hydroxymethyl)tricyclo[5.2.1.0$^{2,6}$]decane is commercially available, for example as the dicidol mixture of the isomeric compounds 3,8-bis(hydroxymethyl)tricyclo [5.2.1.0$^{2,6}$]decane and 4,8-bis(hydroxymethyl)tricyclo [5.2.1.0$^{2,6}$]decane, and also 3,9-bis(hydroxymethyl)tricyclo [5.2.1.0$^{2,6}$]decane and 4,9-bis(hydroxymethyl)tricyclo [5.2.1.0$^{2,6}$]decane.

The bis(hydroxymethyl)tricyclo[5.2.1.0$^{2,6}$]decanes can be synthesized proceeding from dicyclopentadiene (tricyclo [5.2.1.0$^{2,6}$]deca-3,8-diene). Dicyclopentadiene is preparatively readily available in a Diels-Alder reaction by dimerization of cyclopentadiene.

Hydroformylation of dicyclopentadiene then gives bis(hydroxymethyl)tricyclo[5.2.1.0$^{2,6}$]decane. According to the synthesis route, it is possible to selectively obtain bis(hydroxymethyl)tricyclo[5.2.1.0$^{2,6}$]decanes substituted at different positions. For instance, publications JP 7-206740, EP 1 112 995 B1 or EP 0 049 631 B1 specify methods by which, for example, 8,9-bis(hydroxymethyl)tricyclo[5.2.1.0$^{2,6}$]decane is preparable. DE 103 52 260 B3, in contrast, describes processes for preparing 3(4),8(9)-bis(hydroxymethyl)-tricyclo[5.2.1.0$^{2,6}$]decane. The 3(4),8(9) notation of the positions of the hydroxymethyl groups means 3 or 4, 8 or 9.

Bis(hydroxymethyl)tricyclo[5.2.1.0$^{2,6}$]decane, which is commercially available and is usable as a starting compound for preparation of inventive monomers, thus contains hydroxymethyl groups both at position 3 or 4 and at position 8 or 9. It is then possible to synthesize the corresponding polyetherpolyols by addition of alkylene oxides, generally in amounts of 1 to 10 mol, especially of ethylene oxide, propylene oxide, butylene oxide, etc., in the presence of basic catalysts by known methods. EP 0 023 686 B1 contains exact preparation methods for this purpose.

The base-catalyzed reaction of bis(hydroxymethyl)-tricyclo[5.2.1.0$^{2,6}$]decane with ethylene oxide leads, after aqueous workup, to the ethoxylated TCD polyether shown. The alkoxylated TCD diols are of good suitability as a plasticizer in dental polymer matrices.

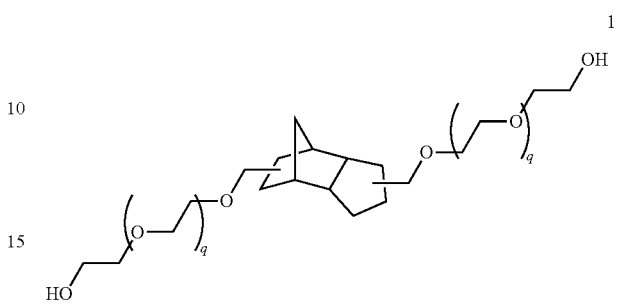

The terminal hydroxyl function can subsequently be esterified, for example, with acetic anhydride to obtain the ethoxylated ester of the above-described TCD polyether.

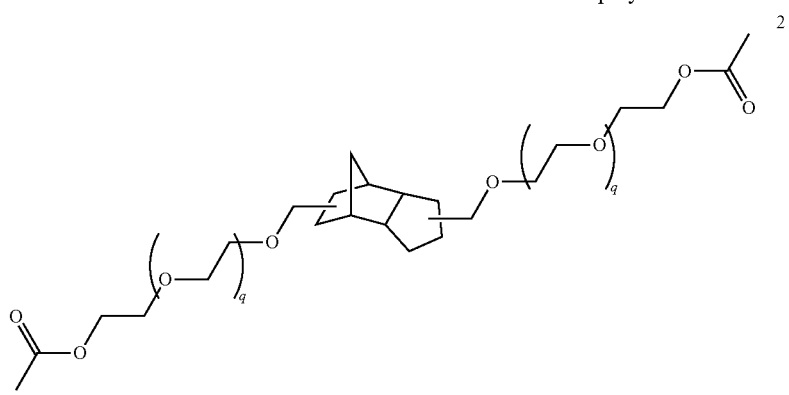

Suitable plasticizers can also be prepared by esterifying bis(hydroxymethyl)tricyclo[5.2.1.0$^{2,6}$]decane with aleuritic acid. The corresponding structure is shown below.

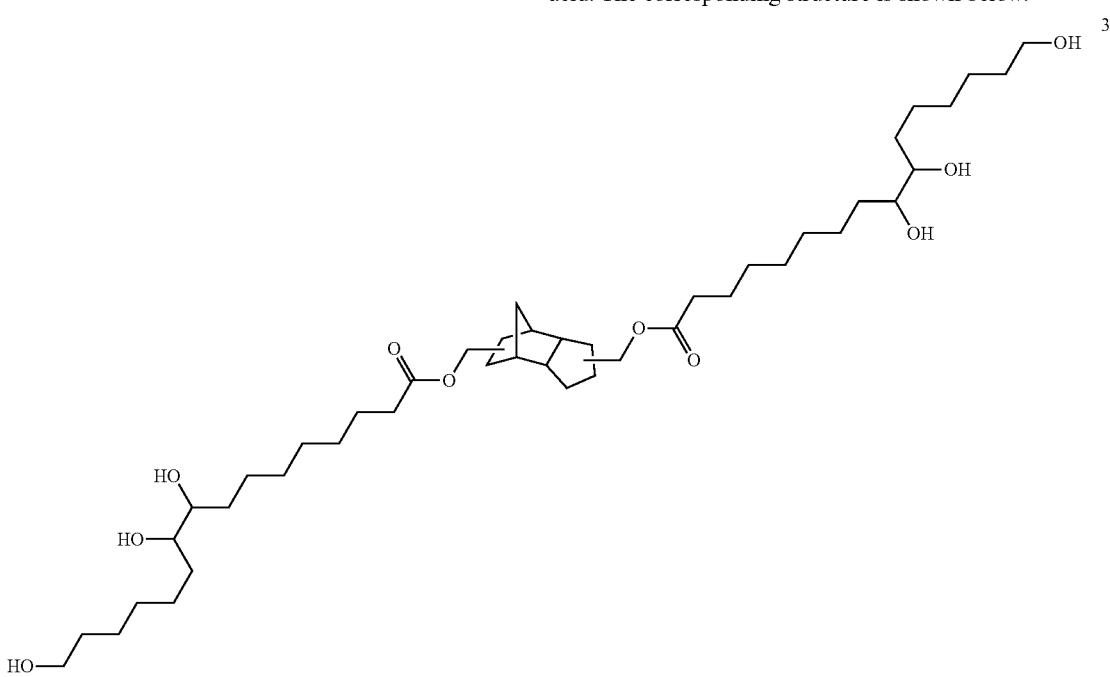

Reaction of bis(hydroxymethyl)tricyclo[5.2.1.0$^{2,6}$]decane with two equivalents of 9-decenoic acid leads to the corresponding diester, which can then be oxidized to the corresponding diketone under palladium catalysis based on what is known as the Wacker process.

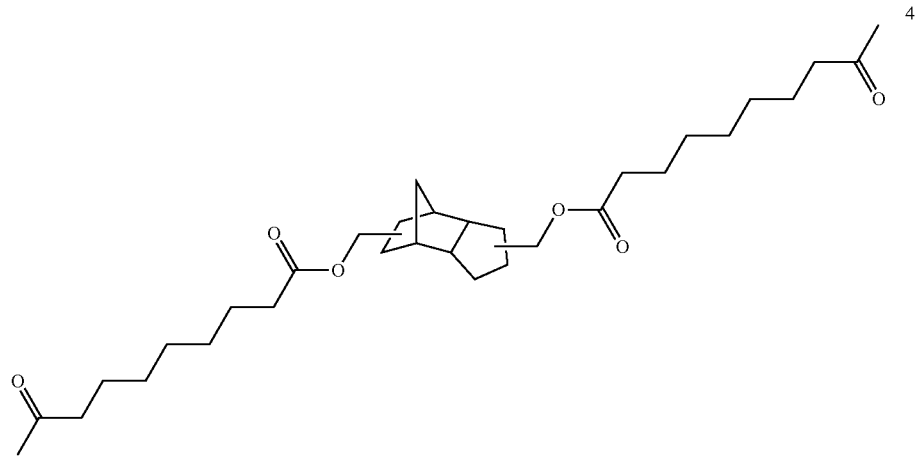

4

Reaction of bis(hydroxymethyl)tricyclo[5.2.1.0$^{2,6}$]decane with acetic anhydride in the presence of catalytic amounts of concentrated sulfuric acid gives 3(4),8(9) bis(acetyloxymethyl)tricyclo[5.2.1.0$^{2,6}$]decane.

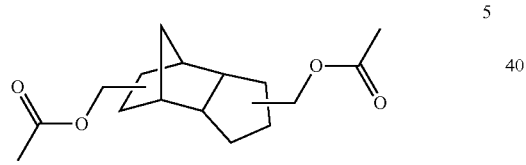

5

Reaction of bis(hydroxymethyl)tricyclo[5.2.1.0$^{2,6}$]decane or the alkoxylated compound thereof with an alkyl halide in the presence of a strong base gives the 3(4),8(9)-bisalkyl methyl ether of tricyclo[5.2.1.0$^{2,6}$]decane or the alkoxylated equivalent thereof.

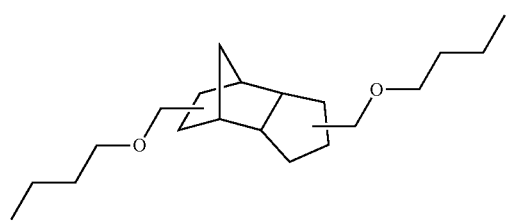

6

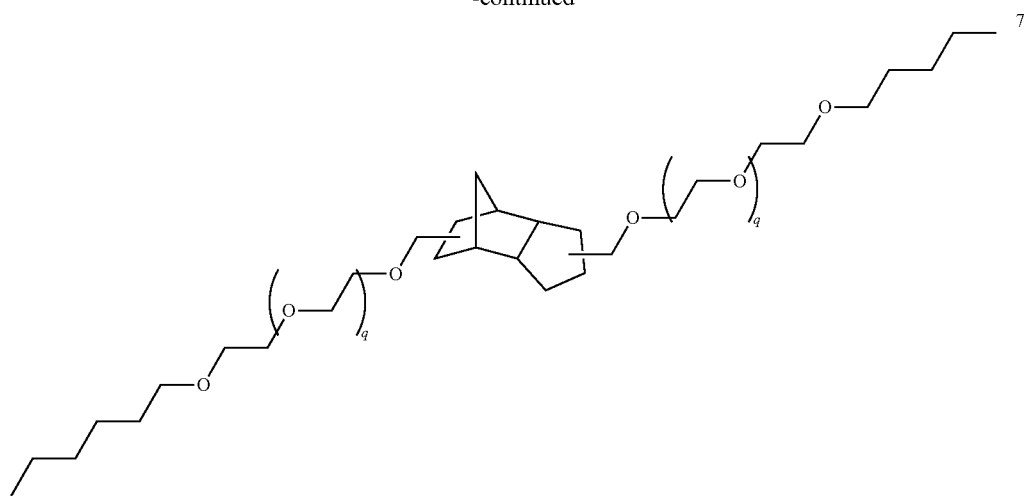
7
Reaction of bis(hydroxymethyl)tricyclo[5.2.1.0$^{2,6}$]decane or the alkoxylated compound thereof with an isocyanate, for example with ethyl 3-isocyanatopropionate, under the conditions of the isocyanate alcohol addition method, in a stoichiometric reaction regime, leads to the corresponding urethane or the alkoxylated equivalent thereof.
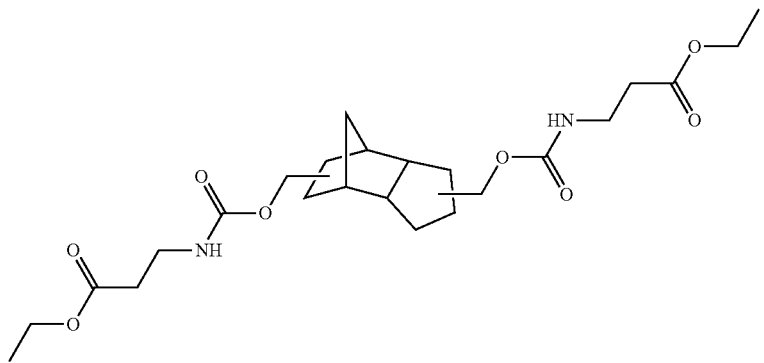
8
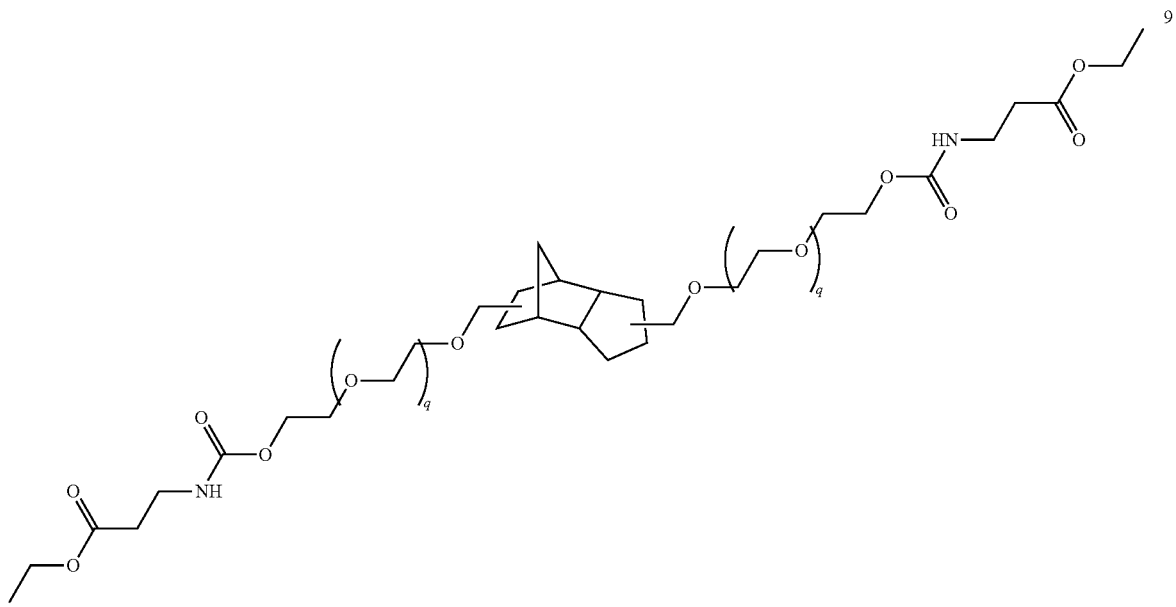
9

Suitable components for use in the isocyanate addition methods may, for example, also be the following commercially available isocyanates: ethyl 2-isocyanatoacetate, methyl 6-isocyanatohexanoate, ethyl 2-isocyanato-3-methylbutyrate, diethyl 2-isocyanatoglutarate, butyl 4-isocyanatobenzoate, ethyl 2-isocyanatobenzoate, 2-isocyanatoethyl propionate, 1-isocyanato-2-methoxyethane, 1-isocyanato-3-methoxy propane, 1-isocyanato-3-isopropoxypropane, 2-(isocyanatomethyl)tetrahydrofuran, (2-isocyanatoethyl)dimethylamine, 3-isocyanatopropanoyl chloride, 3-(isocyanatomethyl)dihydropyrimidine-2,4(1H,3H)-dione.

The stoichiometric reaction products of The stoichiometric reaction products of bis(hydroxymethyl)tricyclo[5.2.1.0$^{2,6}$]decane or of the alkoxylated compound thereof with ethyl 3-isocyanatopropionate under the conditions of the isocyanate-alcohol addition method lead to urethanes which still have reactive hydrogen atoms in the urethane function —O—C(=O)—NH—. These hydrogen atoms can be depleted by further reaction with isocyanates in a second reaction stage. Viewed in formal terms, these addition reactions proceed in such a way that a proton is transferred from the H-active compound to the nitrogen of the isocyanate group and then the resulting negative ion of the adding species binds to the positively polarized carbonyl carbon of isocyanate.

Thus, if bis(hydroxymethyl)tricyclo[5.2.1.0$^{2,6}$]decane or the alkoxylated compound thereof reacts, for example, with two equivalents of ethyl 3-isocyanatopropionate and the temperature regime is adapted, since the further reaction of the second reaction stage generally proceeds at relatively high temperatures, the corresponding allophanate is formed.

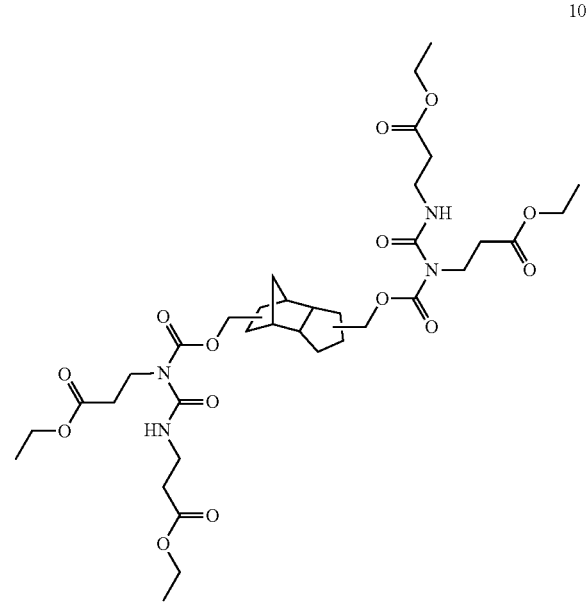

10

Particularly preferred plasticizers are those which result from mixtures whose stoichiometry is between that of the reaction of the alcohol with the isocyanate to give a urethane and to give an allophanate.

Regarding the structure of the allophanate, further reactive hydrogen atoms are also present therein, which are capable of reactions with isocyanates. Products from these third reaction stages of the isocyanate-alcohol reactions are not preferred in the context of this invention.

Single reaction of bis(hydroxymethyl)tricyclo-[5.2.1.0$^{2,6}$]decane, for example with alkyl isocyanate, leads to the corresponding urethane, which affords the corresponding allophanate through further reaction, for example with the alkyl isocyanate.

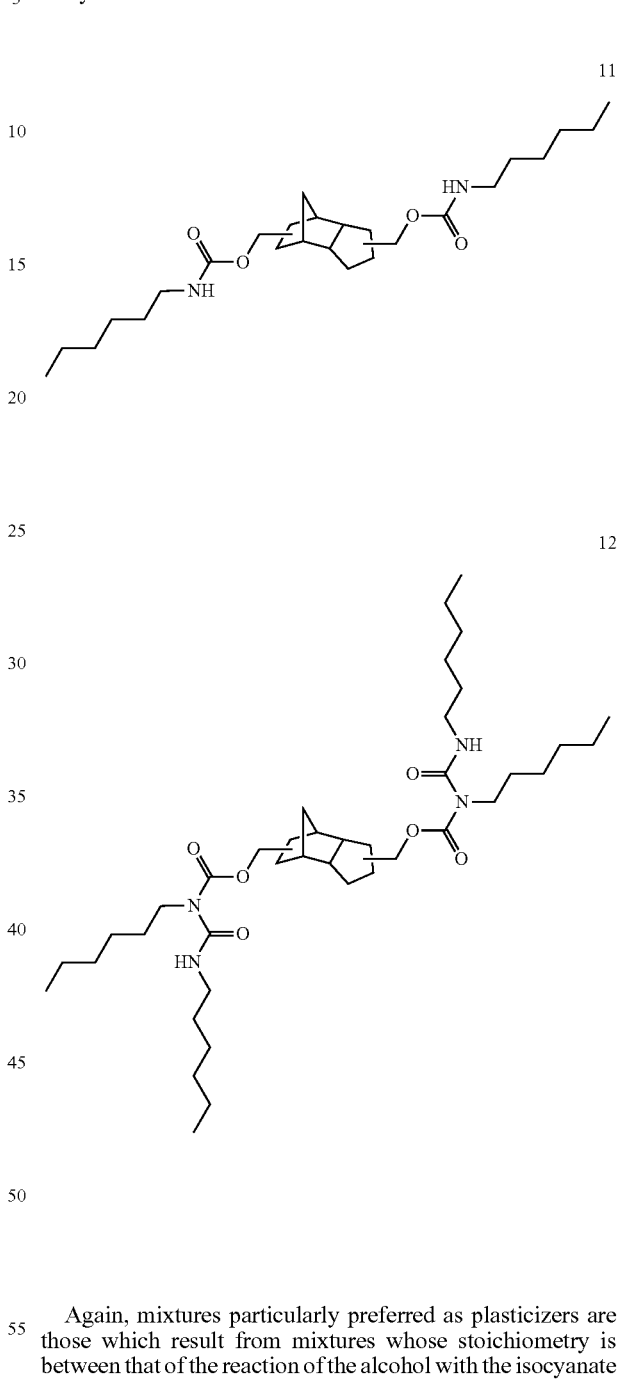

Again, mixtures particularly preferred as plasticizers are those which result from mixtures whose stoichiometry is between that of the reaction of the alcohol with the isocyanate to give a urethane and to give an allophanate, or in which the urethane is not completely reacted in a second reaction stage to give the allophanate.

II. Synthesis of the Plasticizers Proceeding from Carboxylic Acid Derivatives

3(4),8(9)-bis(Carboxylic acid)tricyclo[5.2.1.0$^{2,6}$]decane can be prepared by simple oxidation of the commercially available 3(4),8(9)-bis(formyl)tricyclo[5.2.1.0$^{2,6}$]-decane.

Reaction of the dicarboxylic acid with ethanol in the presence of catalytic amounts of concentrated sulfuric acid leads to ethyl tricyclo[5.2.1.0$^{2,6}$]decane-3 (4),8(9)-dicarboxylate.

13

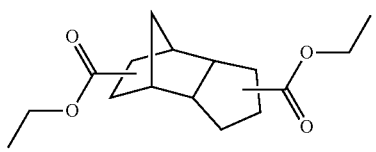

Reaction of 3(4),8(9)-bis(carboxylic acid)tricyclo-[5.2.1.0²,⁶]decane, for example, with ethyl 3-isocyanatopropionate under the specific conditions of this addition process gives the corresponding amide.

14

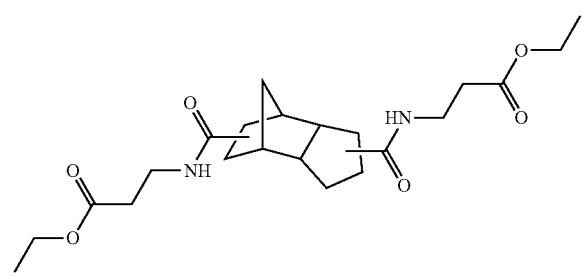

If the amide which originates from the stoichiometric reaction of 3(4),8(9)-bis(carboxylic acid)tricyclo[5.2.1.0²,⁶]decane with ethyl 3-isocyanatopropionate is reacted further in a second reaction stage, likewise stoichiometrically, for example, with an isocyanate, the corresponding acylurea is obtained.

15

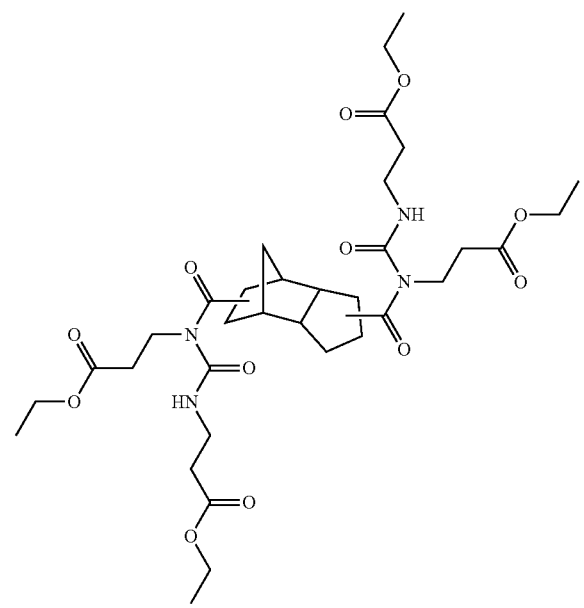

Here too, particularly preferred plasticizers are those mixtures which result from mixtures whose stoichiometry is between that of the reaction of a carboxylic acid with an isocyanate to give an amide and to give an acylurea.

Reaction of 3(4),8(9)-bis(carboxylic acid)tricyclo[5.2.1.0²,⁶]decane with thionyl chloride to give the carbonyl chloride and further reaction of the carbonyl chloride with an amine gives the corresponding amide by elimination of HCl.

16

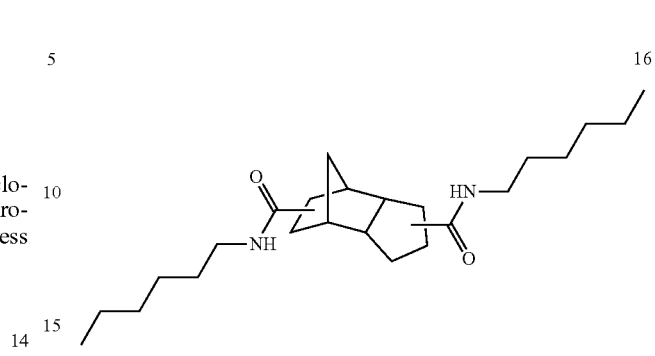

Alternatively, the amide can be obtained by reaction of 3(4),8(9)-bis(carboxylic acid)tricyclo[5.2.1.0²,⁶]decane with an alkyl isocyanate.

Further reaction of the amide, for example with an alkyl isocyanate, leads to the corresponding acylurea.

17

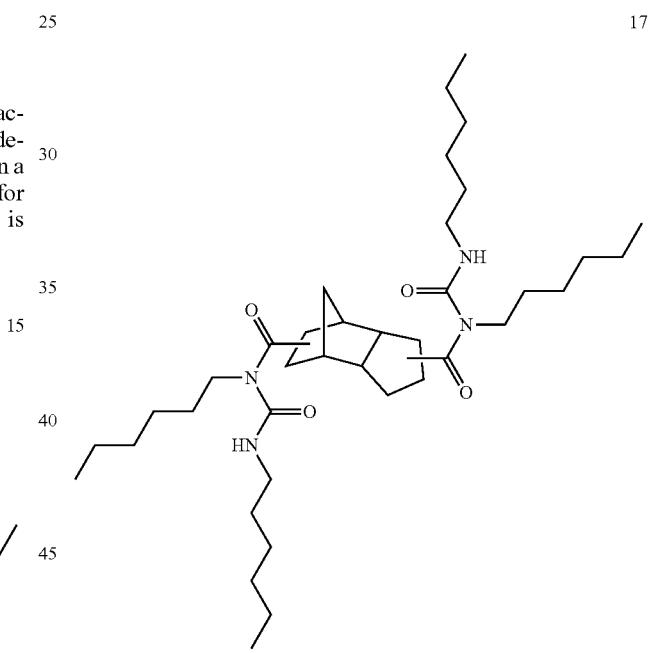

III. Synthesis of the Plasticizers Proceeding from Amines

3(4),8(9)-bis(aminomethyl)tricyclo[5.2.1.0²,⁶]decane is known per se or can be prepared, for example, by reacting the corresponding tosylates with ammonia. If the amine is reacted gradually with methyl acrylate, this gives, according to the reaction stoichiometry of this vinylogenic addition, the corresponding Michael-like adducts.

18

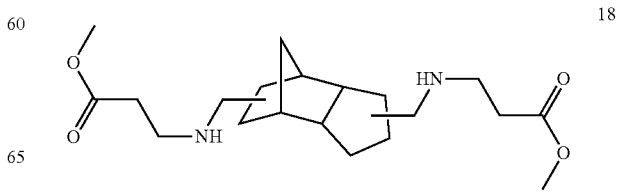

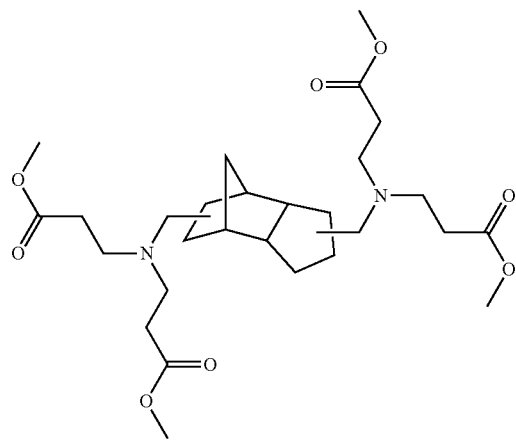

19

Reaction of 3(4),8(9)-bis(aminomethyl)tricyclo[5.2.1.0$^{2,6}$]decane for example with ethyl 3-isocyanatopropionate, under the conditions of the isocyanate addition method, leads to the corresponding urea.

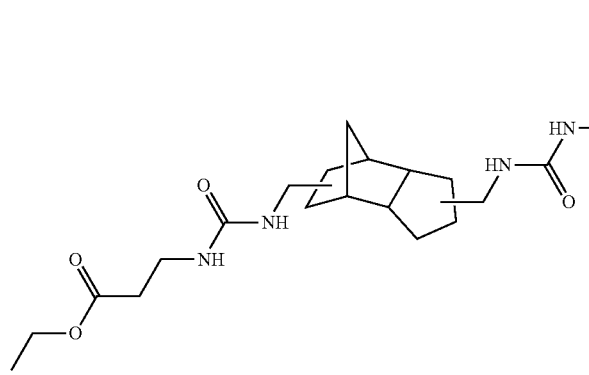

20

If 3(4),8(9)-bis(aminomethyl)tricyclo[5.2.1.0$^{2,6}$]decane is reacted with two equivalents of ethyl 3-isocyanatopropionate, this gives the corresponding biurets.

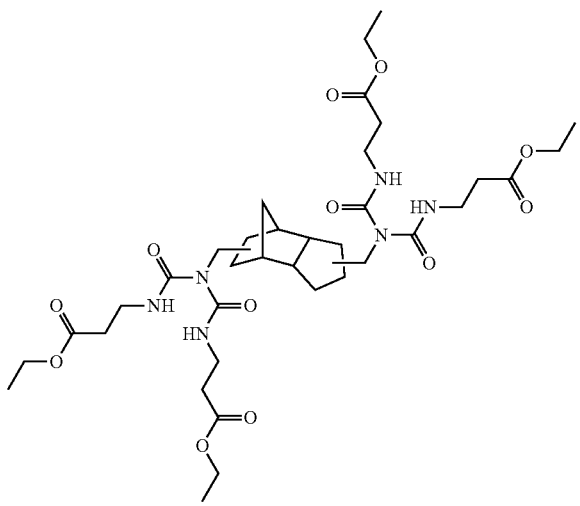

22

Here too, particularly preferred plasticizers are those mixtures which result from mixtures whose stoichiometry is between that of the reaction of an amine with an isocyanate to give a urea and to give a biuret.

For further illustration of suitable plasticizers, for example, the reaction products of 3(4),8(9)-bis(aminomethyl)tricyclo[5.2.1.0$^{2,6}$]decane with alkyl halides under basic conditions are useful. According to the stoichiometry of the mixture, this gives the corresponding amines.

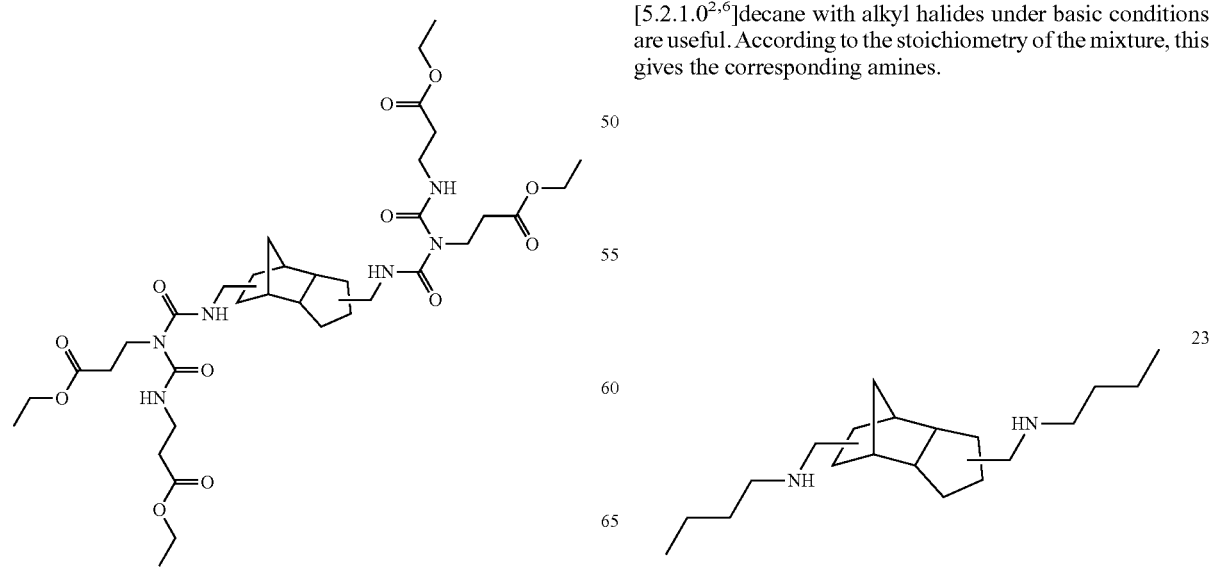

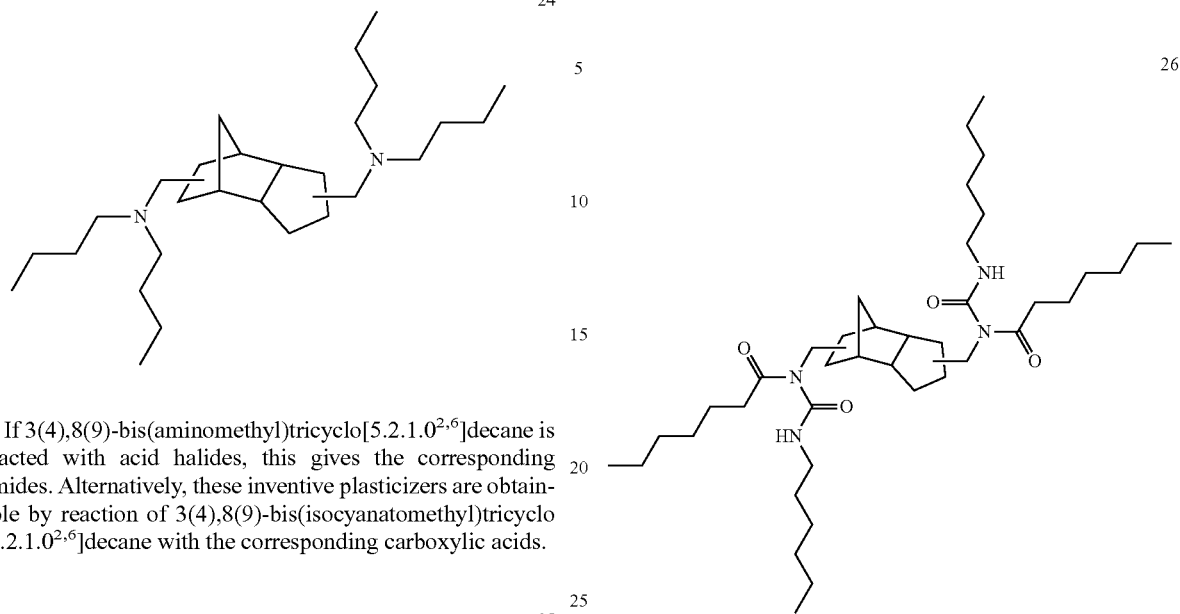

If 3(4),8(9)-bis(aminomethyl)tricyclo[5.2.1.0$^{2,6}$]decane is reacted with acid halides, this gives the corresponding amides. Alternatively, these inventive plasticizers are obtainable by reaction of 3(4),8(9)-bis(isocyanatomethyl)tricyclo[5.2.1.0$^{2,6}$]decane with the corresponding carboxylic acids.

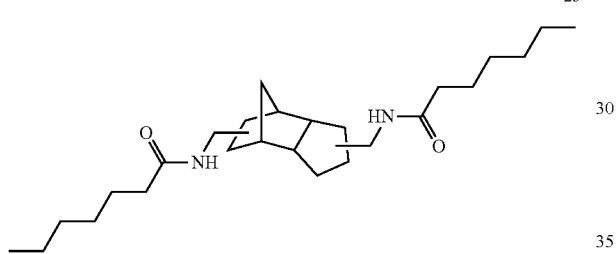

If the above amide is reacted, for example, with an alkyl isocyanate, this gives the corresponding acylurea.

Reaction of 3(4),8(9)-bis(aminomethyl)tricyclo[5.2.1.0$^{2,6}$]decane with an alkyl isocyanate leads, like the reaction of 3(4),8(9)-bis(isocyanatomethyl)-tricyclo[5.2.1.0$^{2,6}$]decane with the corresponding amine too, to the ureas, which can then be reacted further, for example with alkyl isocyanate.

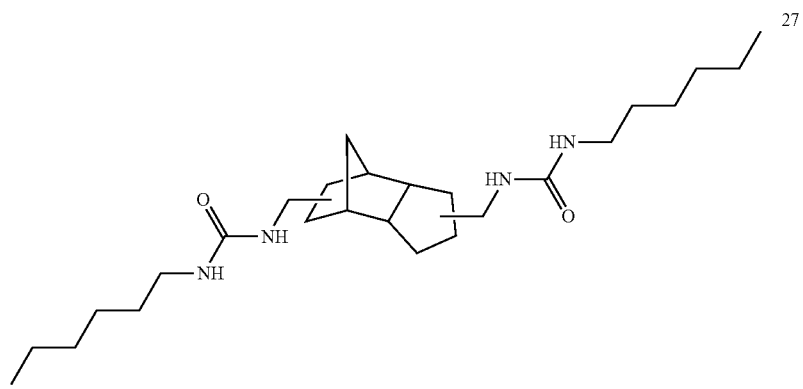

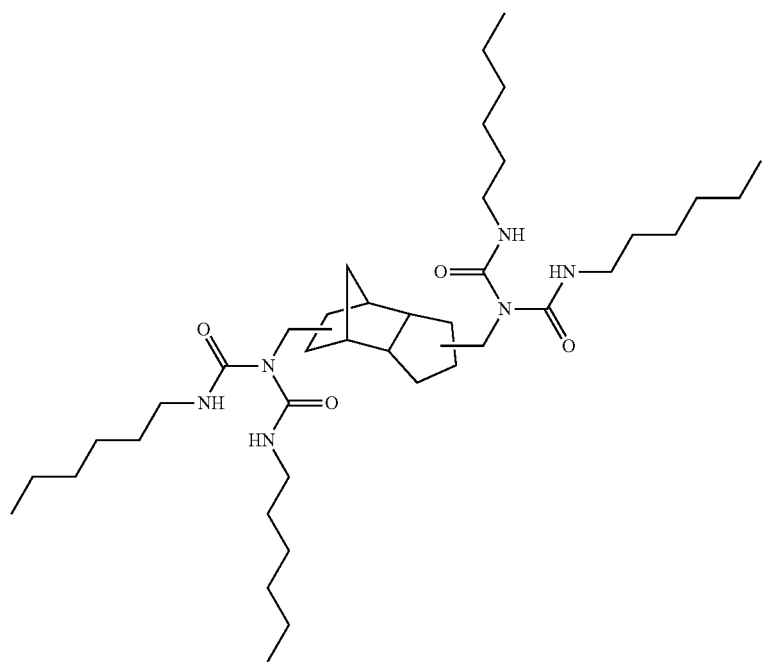

Reaction of 3(4),8(9)-bis(aminomethyl)tricyclo[5.2.1.0$^{2,6}$]decane, for example with ethylene oxide, gives the once- or twice-substituted alkoxylated amino alcohol, which can then be esterified, for example, by reaction with acetic anhydride.

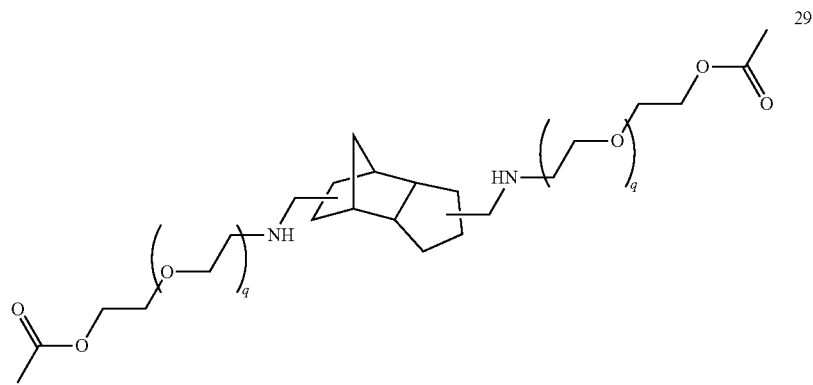

IV. Synthesis of the Plasticizers Proceeding from Isocyanates

3(4),8(9)-bis(isocyanatomethyl)tricyclo[5.2.1.0$^{2,6}$]decane is known per se and is one of the conventional diisocyanate compounds used in industrial applications (see DE 37 03 120 A1 and WO 2009/065873 A2). Conversion of this compound under the conditions of the isocyanate-alcohol addition method, for example with methyl 3-hydroxypropanoate, leads to the corresponding urethane.

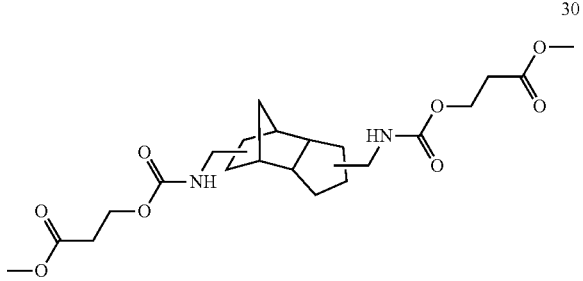

If, rather than methyl 3-hydroxypropanoate, an alkoxylated version is used, this gives the correspondingly alkoxylated urethane.

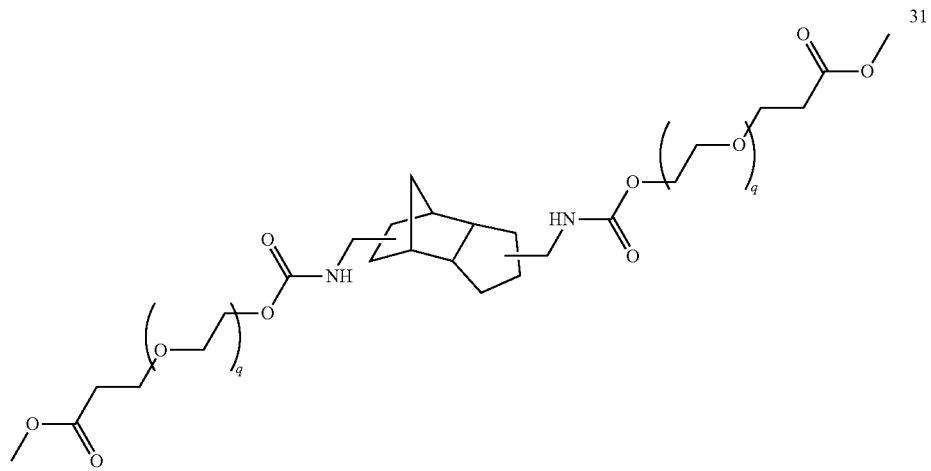

If, for example, an amino alcohol is reacted with the 3(4),8(9)-bis(isocyanatomethyl)tricyclo[5.2.1.0$^{2,6}$]decane, the resulting alcohol is alkoxylated and this compound is then reacted with acetic anhydride, this gives the correspondingly alkoxylated urea compound.

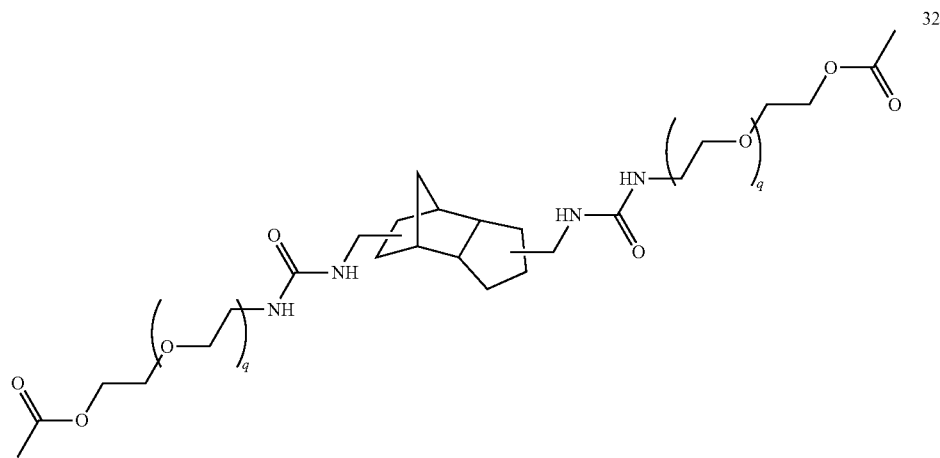

Reaction of 3(4),8(9)-bis(isocyanatomethyl)tricyclo-[5.2.1.0$^{2,6}$]decane, for example with the commercially available monomethyl succinate, under the specific conditions of the addition reaction of a carboxylic acid with an isocyanate, gives the corresponding amide.

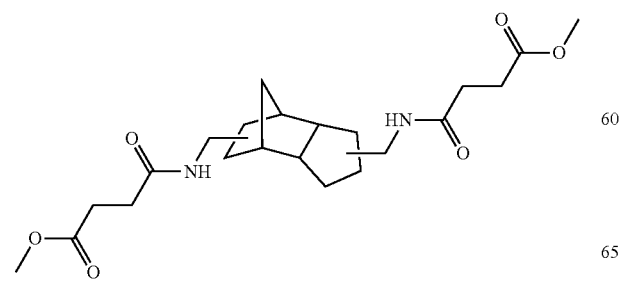

Alternatively, it is also possible to react the urethane obtainable from the stoichiometric reaction of 3(4),8(9)-bis(isocyanatomethyl)tricyclo[5.2.1.0$^{2,6}$]decane with methyl 3-hydroxypropanoate or the alkoxylated representative thereof with further isocyanate compounds, for example with ethyl 3-isocyanatopropionate, to give the corresponding allophanates.

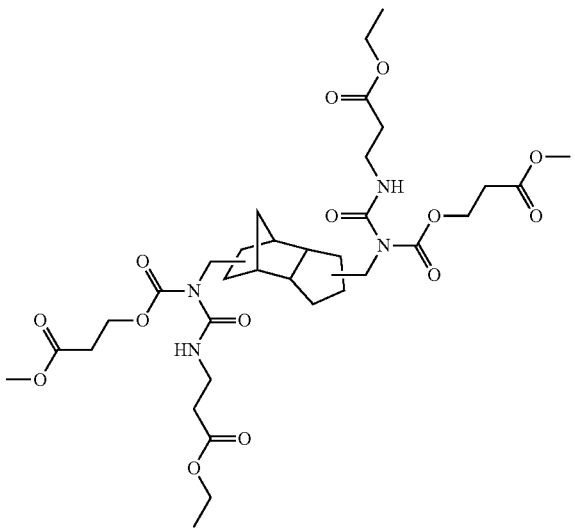

Again, mixtures particularly preferred as plasticizers are those which result from mixtures whose stoichiometry is between that of the reaction of the alcohol with the isocyanate to give a urethane and to give an allophanate, for example in which the urethane in a second reaction stage is not reacted fully to give the allophanate.

Analogously, it is also possible to react the amide which results from the reaction of 3(4),8(9) bis(isocyanatomethyl)tricyclo[5.2.1.0$^{2,6}$]decane with monomethyl succinate in a second reaction stage with an isocyanate, for example ethyl 3-isocyanatopropionate, further to give the corresponding acylurea.

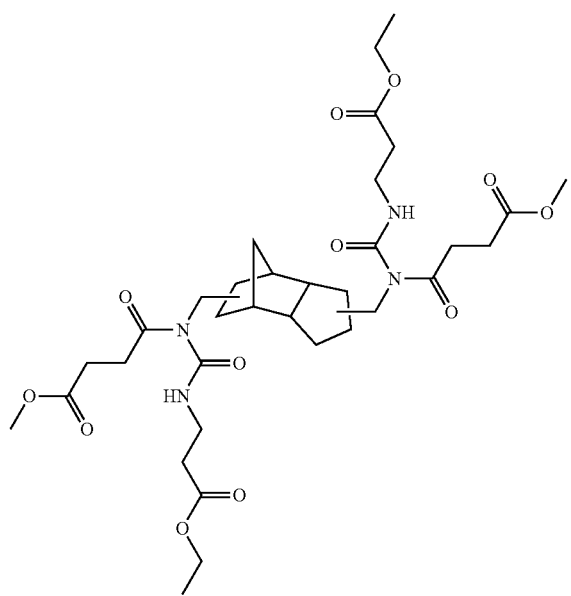

Here too, particularly preferred plasticizers are those mixtures which result from mixtures whose stoichiometry is between that of the reaction of a carboxylic acid with an isocyanate to give an amide and to give an acylurea.

EXAMPLES

3(4),8(9)-bis(acetyloxymethyl)tricyclo[5.2.1.0$^{2,6}$]decane ("TCD" Plasticizer)

10 drops of concentrated sulfuric acid are added to 98.15 g (0.5 mol) of tricyclo[5.2.1.0$^{2,6}$]decane-3(4),8(9)-dimethanol and 102.09 g (1.0 mol) of acetic anhydride, and the mixture is stirred on a rotary evaporator (without vacuum) until a homogeneous solution has formed. This is followed by heating to 100° C. under reflux for 2 h. After cooling, the reaction mixture is added to 300 ml of ice-water and extracted with dichloromethane. The combined organic phases are deacidified with sodium carbonate solution and washed with water. The mixture is dried over magnesium sulfate and filtered, and the solvent is removed under reduced pressure. 136.09 g (0.49 mol; 97.1%) of a pale yellow oil are obtained.

$C_{16}H_{24}O_4$ (280.36 g/mol)

Viscosity: 136.8 cSt $n^D 20$: 1.487

IR (film; cm$^{-1}$): 2946 (m, $v_{C-H}$); 1735 (vs, $v_{C=O}$); 1446 (w, $\delta_{C-H}$); 1367 (m, $\delta_{C-H}$, acetyl); 1229 (vs, $v_{C-O}$); 1029 (s)

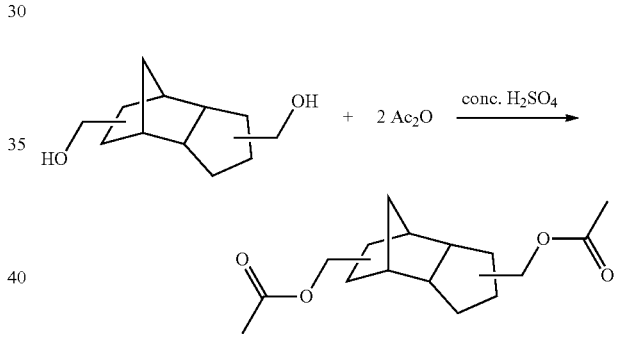

1,3,5-triacetyloxytricyclo[3.3.1.1$^{3,7}$]decane ("adamantane" Plasticizer)

92.12 g (0.5 mol) of 1,3,5-adamantanetriol are suspended in 153.14 g (1.5 mol) of acetic anhydride. Subsequently, 10 drops of concentrated sulfuric acid are added and the mixture is stirred on a rotary evaporator (without vacuum) until a homogeneous solution has formed. Subsequently, the mixture is heated to 100° C. under reflux for 2 h. After cooling, the reaction mixture is added to 300 ml of ice-water and extracted with dichloromethane. The combined organic phases are deacidified with sodium carbonate solution and washed with water. The mixture is dried over magnesium sulfate and filtered, and the solvent is removed under reduced pressure. 150.50 g (0.48 mol; 97.0%) of a colorless oil are obtained.

$C_{16}H_{22}O_6$ (310.35 g/mol)

$n^D 20$: 1.485

IR (film; cm$^{-1}$): 2935 (m, $v_{C-H}$); 1730 (vs, $v_{C=O}$); 1463 (w, $\delta_{C-H}$); 1434 (w, $\delta_{C-H}$); 1366 (m, $\delta_{C-H}$, acetyl); 1220 (vs, $v_{C-O}$); 1018 (s)

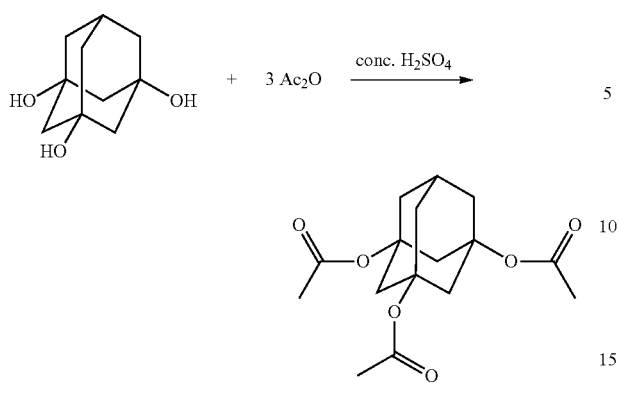

Ethyl tricyclo[5.2.1.0$^{2,6}$]decane-3(4),8(9)-dicarboxylate ("Ester" Plasticizer)

112.13 g (0.5 mol) of tricyclo[5.2.1.0$^{2,6}$]decane-3(4),8(9)-dicarboxylic acid and 80.62 g (1.75 mol) of ethanol are heated with 5 g of conc. sulfuric acid in 100 ml of chloroform under reflux on a water separator until no further water separates out. After cooling, the reaction solution is washed with water, hydrogencarbonate solution and water. The mixture is dried over magnesium sulfate and filtered, and the solvent is removed under reduced pressure. 126.21 g (0.45 mol; 90.0%) of a colorless oil are obtained.

$C_{16}H_{24}O_4$ (280.36 g/mol)

$n^D 20$: 1.487

IR (film; cm$^{-1}$): 2940 (m, $v_{C-H}$); 1740 (vs, $v_{C=O}$); 1452 (w, $\delta_{C-H}$); 1377 (m, $\delta_{C-H}$); 1221 (vs, $v_{C-O}$); 1025 (s)

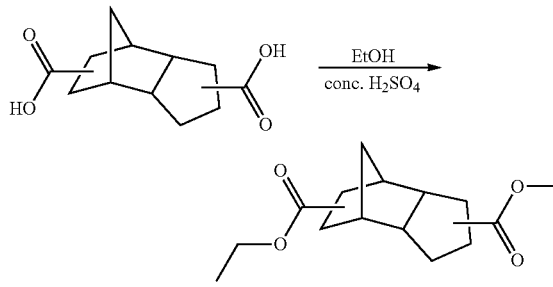

Michael adduct of 3(4),8(9)-bis(aminomethyl)tricyclo-[5.2.1.0$^{2,6}$]decane and methyl acrylate ("Michael" Plasticizer)

172.18 g (2.0 mol) of methyl acrylate are added gradually to 97.16 g (0.5 mol) of 3(4),8(9) bis(aminomethyl)tricyclo[5.2.1.0$^{2,6}$]decane and the mixture is stirred at room temperature for 2 h. The reaction is monitored by IR (disappearance of the acrylate band at 1630 cm$^{-1}$).

$C_{28}H_{46}O_8N_2$ (538.68 g/mol)

$n^D 20$: 1.497

IR (film; cm$^{-1}$): 2935 (s, $v_{C-H}$); 1733 (vs, $v_{C=O}$); 1439 (m, $\delta_{C-H}$); 1359 (m, $\delta_{C-H}$); 1171 (vs, $v_{C-O}$); 1016 (m)

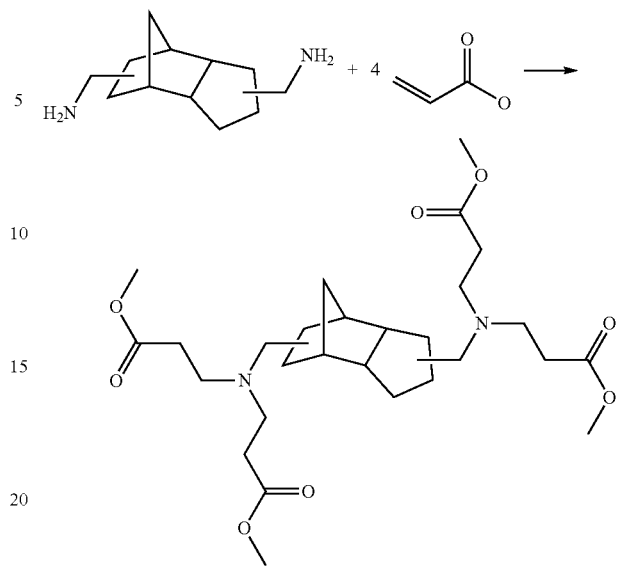

Reaction product of tricyclo[5.2.1.0$^{2,6}$]decane-3(4),8(9)-dimethanol and ethyl 3-isocyanatopropionate ("Urethane" Plasticizer)

143.14 g (1.0 mol) of ethyl 3-isocyanatopropionate and 2.99 g (0.015 mol) of phenothiazine are dissolved in 250 ml of toluene and heated to 70° C. Then 3.51 g (0.01 mol) of zinc octoate are added. Subsequently, 98.15 g (0.5 mol) of tricyclo[5.2.1.0$^{2,6}$]decane-3(4),8(9)-dimethanol in 150 ml of tetrahydrofuran are slowly added dropwise. Thereafter, 6.76 g (0.05 mol) of dimethylbenzylamine are added and the mixture is stirred at 70° C. overnight. The reaction is monitored by IR (disappearance of the isocyanate band at 2270 cm$^{-1}$). The solvent is removed under reduced pressure to obtain 236.65 g (0.49 mol, 97.2%) of a colorless oil.

$C_{24}H_{42}N_2O_8$ (486.60 g/mol)

$n^D 20$: 1.498

IR (film; cm$^{-1}$): 3356 (m, $v_{N-H}$), 2945 (s, $v_{C-H}$); 1712 (vs, $v_{C=O}$), 1695 (vs, $v_{C=O}$), 1522 (m, $\delta_{N-H}$), 1452 (m, $\delta_{C-H}$); 1374 (m, $\delta_{C-H}$); 1243 (s, $v_{C-O}$), 1182 (vs, $v_{C-O}$); 1017 (s)

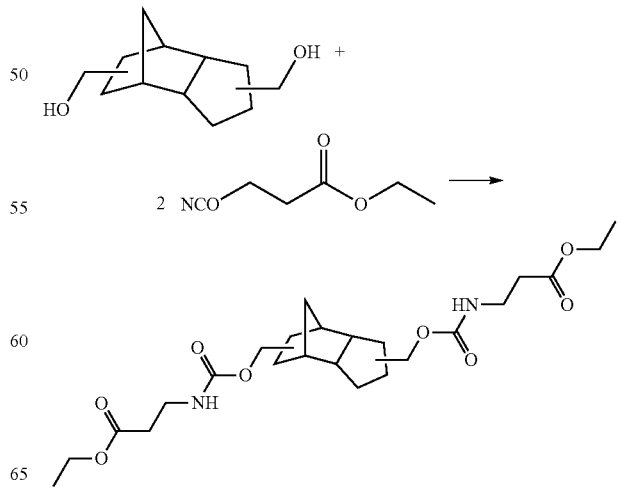

Reaction product of 3(4),8(9)-bis(aminomethyl)tricyclo-[5.2.1.0$^{2,6}$]decane and ethyl 3-isocyanatopropionate ("Urea" Plasticizer)

143.14 g (1.0 mol) of ethyl 3-isocyanatopropionate and 2.99 g (0.015 mol) of phenothiazine are dissolved in 250 ml of toluene and the mixture is heated to 70° C. Then 3.51 g (0.01 mol) of zinc octoate are added. Subsequently, 97.16 g (0.5 mol) of 3(4),8(9) bis(aminomethyl)tricyclo[5.2.1.0$^{2,6}$]decane in 150 ml of toluene are slowly added dropwise. Thereafter, 6.76 g (0.05 mol) of dimethylbenzylamine are added and the mixture is stirred at 70° C. overnight. The reaction is monitored by IR (disappearance of the isocyanate band at 2270 cm$^{-1}$). The solvent is removed under reduced pressure to obtain 241.33 g (0.48 mol, 95.2%) of a colorless oil.

$C_{24}H_{44}N_4O_6$ (506.64 g/mol)
$n^D 20$: 1.498

IR (film; cm$^{-1}$): 3333 (m, $v_{N-H}$), 2938 (s, $v_{C-H}$); 1732 (s, $v_{C=O}$, ester); 1631 (s, $v_{C=O}$, urea), 1564 (vs, $\delta_{N-H}$), 1460 (w, $\delta_{C-H}$); 1374 (w, $\delta_{C-H}$); 1247 (s, $v_{C-O}$), 1179 (vs, $v_{C-O}$); 1030 (m)

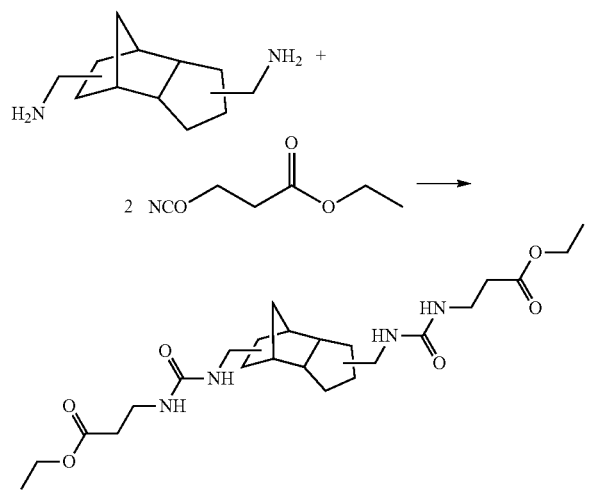

Abbreviations:
UDMA: urethane dimethacrylate
BisEMA: ethoxylated bisphenol A dimethacrylate
TCD-DMA: bis(methacryloyloxymethyl)tricyclo [5.2.1.0$^{2,6}$]decane
BisGMA: bisphenol A glycidyl dimethacrylate
TEDMA: triethylene glycol dimethacrylate
BAP: 2,2-bis-4-(2-acetyloxyethoxyphenyl)propane
GK: silanized glass ceramic (GM27884, Schott)
DEPT: N,N-dihydroxyethyl-p-toluidine
BHT: 3,5-di-tert-butyl-4-hydroxytoluene
BPO: dibenzoyl peroxide
Temporary C&B material (10:1)

TABLE 1

| Base pastes (temporary C&B material) | | |
| --- | --- | --- |
|  | Base 1 | Base 2 |
| UDMA | 19.00 | 28.40 |
| BisEMA | 38.00 | 0.00 |
| TCD-DMA | 0.00 | 28.40 |
| GK | 35.95 | 35.95 |
| Aerosil A300 | 1.50 | 1.50 |
| Aerosil R812 | 3.00 | 3.00 |
| DEPT | 2.50 | 2.70 |
| BHT | 0.05 | 0.05 |

TABLE 2

| Catalyst pastes (temporary C&B material) | | | | |
| --- | --- | --- | --- | --- |
|  | Cat 1 | Cat 2 | Cat 3 | Cat 4 |
| BAP | 53.50 | 0.00 | 0.00 | 0.00 |
| "TCD" plasticizer | 0.00 | 53.50 | 0.00 | 0.00 |
| "Adamantane" plasticizer | 0.00 | 0.00 | 53.50 | 0.00 |
| "Ester" plasticizer | 0.00 | 0.00 | 0.00 | 53.50 |
| GK | 36.60 | 36.60 | 36.60 | 36.60 |
| Aerosil A300 | 1.50 | 1.50 | 1.50 | 1.50 |
| Aerosil R812 | 3.00 | 3.00 | 3.00 | 3.00 |
| BPO | 5.40 | 5.40 | 5.40 | 5.40 |

|  | Cat 5 | Cat 6 | Cat 7 |
| --- | --- | --- | --- |
| "Michael" plasticizer | 53.50 | 0.00 | 0.00 |
| "Urethane" plasticizer | 0.00 | 53.50 | 0.00 |
| "Urea" plasticizer | 0.00 | 0.00 | 53.50 |
| GK | 36.60 | 36.60 | 36.60 |
| Aerosil A300 | 1.50 | 1.50 | 1.50 |
| Aerosil R812 | 3.00 | 3.00 | 3.00 |
| BPO | 5.40 | 5.40 | 5.40 |

TABLE 3

Examples (temporary C&B materials, 10:1)

| | Example | | | |
| --- | --- | --- | --- | --- |
| | 1 | 2 | 3 | 4 |
| Base paste | 1 | 1 | 1 | 1 |
| Catalyst paste | 1 | 2 | 3 | 4 |
| Setting time | 102 s | 99 s | 102 s | 100 s |
| Working time | 63 s | 66 s | 69 s | 66 s |
| Water absorption | 20.1 μg/mm³ | 17.2 μg/mm³ | 17.5 μg/mm³ | 17.5 μg/mm³ |
| Solubility | 4.4 μg/mm³ | 1.4 μg/mm³ | 1.4 μg/mm³ | 1.5 μg/mm³ |
| Flexural strength (1 h) | 63.5 MPa | 67.8 MPa | 67.3 MPa | 66.4 MPa |
| Flexural strength (24 h) | 90.7 MPa | 111.2 MPa | 111.1 MPa | 109.1 MPa |

| | Example | | | |
| --- | --- | --- | --- | --- |
| | 5 | 6 | 7 | 8 |
| Base paste | 1 | 1 | 1 | 1 |
| Catalyst paste | 5 | 6 | 7 | 8 |
| Setting time | 102 s | 104 s | 105 s | 102 s |
| Working time | 72 s | 74 s | 74 s | 51 s |
| Water absorption | 18.3 μg/mm³ | 18.5 μg/mm³ | 19.4 μg/mm³ | 10.5 μg/mm³ |

TABLE 3-continued

Examples (temporary C&B materials, 10:1)

| Solubility | 1.8 µg/mm³ | 1.9 µg/mm³ | 2.1 µg/mm³ | 0.8 µg/mm³ |
|---|---|---|---|---|
| Flexural strength (1 h) | 66.6 MPa | 66.1 MPa | 65.9 MPa | 75.8 MPa |
| Flexural strength (24 h) | 110.5 MPa | 110.9 MPa | 109.3 MPa | 111.8 MPa |

Relining Material (10:1)

TABLE 4

Base pastes (relining material)

| | Base 3 | Base 4 |
|---|---|---|
| BisGMA | 18.00 | 0.00 |
| TEDMA | 10.00 | 3.00 |
| UDMA | 10.00 | 12.95 |
| TCD-DMA | 0.00 | 22.00 |
| GK | 55.85 | 55.85 |
| Aerosil R812 | 4.20 | 4.20 |
| Aerosil A300 | 1.40 | 1.40 |
| DEPT | 0.50 | 0.55 |
| BHT | 0.05 | 0.05 |

TABLE 5

Catalyst pastes (relining material)

| | Cat 9 | Cat 10 |
|---|---|---|
| BAP | 53.00 | 0.00 |
| "TCD" plasticizer | 0.00 | 53.00 |
| GK | 35.60 | 35.60 |
| Aerosil R812 | 4.80 | 4.80 |
| Aerosil A300 | 1.60 | 1.60 |
| BPO | 5.00 | 5.00 |

TABLE 6

Examples of relining material (10:1)

| | Example | | |
|---|---|---|---|
| | 9 | 10 | 11 |
| Base paste | 3 | 3 | 4 |
| Catalyst paste | 9 | 10 | 10 |
| Setting time | 168 s | 168 s | 148 s |
| Working time | 339 s | 327 s | 297 s |
| Water absorption | 20.2 µg/mm³ | 17.7 µg/mm³ | 11.3 µg/mm³ |
| Solubility | 3.3 µg/mm³ | 1.6 µg/mm³ | 1.0 µg/mm³ |
| Flexural strength (2 × 2) | 71.3 MPa | 80.0 MPa | 85.4 MPa |
| Adhesion on Paladur | 4.6 MPa | 7.7 MPa | 7.9 MPa |

For the production of the base and catalyst pastes of the temporary C&B materials and of the relining materials, the constituents were each weighed in, homogenized in a Speed-Mixer™ DAC 600.1 VAC-P (Hauschild & Co KG, Hamm, Germany), rolled in a three-roll mill (Exakt, Norderstedt, Germany) and then devolatilized at vacuum −0.9 bar on the SpeedMixer™ DAC 600.1 VAC-P.

The temporary C&B materials and relining materials were dispensed into S50 cartridges (50 ml, 10:1, CS 050-10-68, PSA 53-10-SI, PSB 53-10-SI) from Sulzer Mixpac AG (Haag, Switzerland), filling the base paste into the large chamber and the catalyst paste into the small chamber of each of these 10:1 cartridges. For mixing, the appropriate MBX 3.2-16-S static mixers from Sulzer Mixpac AG were placed onto the cartridges and the two components were squeezed out with a dispenser (DS50-10-00) and mixed homogeneously.

In the above reference examples, the BAP plasticizer which is currently being used as standard in dental mixtures was used as the prior art compound. The examples for the temporary C&B material show that, in the case of the inventive use of dental mixtures comprising plasticizers with the structure $Q-[(Y)_n-X]_o$, it is possible to obtain dental materials which feature reduced water absorption and solubility with simultaneously higher mechanical strength compared to the prior art. Moreover, no adverse effect on the processing properties of the dental compositions is observed. The properties are very particularly advantageous in the case of use of a mixture with TCD-DMA/UDMA resin matrix.

The results of the examples for relining material point exactly in the same direction as those for the examples for the temporary C&B material. In addition to the advantages of reduced water absorption and solubility with improved mechanical strengths, increased adhesion values of the relining materials on a prosthetic plastic also occur here.

Infrared spectroscopy (IR): The IR spectra were measured with a Spectrum 100 FT-IR spectrometer (Perkin Elmer, Rodgau, Germany).

Refractive index ($n^D_{20}$): The refractive indices were measured on an RE 40 refractometer (Mettler Toledo, Giessen, Germany).

Viscosity: The viscosities were measured with a CS Lauda/CD15 Lauda/capillary IIc Ubbelohde viscometer (Schott Instruments Analytics GmbH, Mainz, Germany) at 20° C.

Setting time: The setting times were determined on a thermocouple instrument according to ISO 4049.

Working time: The working times were determined on a thermocouple instrument according to ISO 4049.

Water absorption: The water absorptions were determined according to ISO 4049.

Solubility: The solubilities were determined according to ISO 4049.

Flexural strength: The flexural strengths were determined according to ISO 4049. For the temporary C&B materials, in a modification of ISO 4049, test specimens of dimensions (25±2) mm×(5.0±0.1) mm×(5.0±0.1) were produced. In addition to the flexural strengths, 24 hours after commencement of mixing, the flexural strengths were also determined 1 hour after commencement of mixing for the temporary C&B materials.

Adhesion: The adhesion of the relining materials was determined in a shear test on a Zwick Z2.5 universal tester (Zwick GmbH & Co. KG, Ulm, Germany) at a test speed of 1 mm/min. Paladur test specimens with a diameter of 25 mm and a height of 15 mm (Heraeus Kulzer GmbH, Hanau, Germany) were surface-ground (SiC abrasive paper, grit size 180). Ufi gel hard adhesive (VOCO GmbH, Cuxhaven, Germany) was applied to the test specimen surface and left to dry under air for 30 seconds. Subsequently, a mold ring (diameter 8 mm, height 6 mm) was placed onto the surface and filled with the mixed relining material. The samples were cured at (37±1)° C. at 100% air humidity for 24 hours. Subsequently, the mold ring was removed and the adhesion between relining material and Paladur in the shear test was determined as the quotient of the force on fracture and of the adhesion surface.

The invention claimed is:
1. A dental curable composite material comprising
(a) one or more compound(s) of the structure $Q-[(Y)_n-X]_o$ which are not free-radically polymerizable during curing with constituent (b), wherein:

Q is a tricyclic structural element wherein one, two or more of the hydrogen atoms not substituted by $Y_n$-X substituents in this tricyclic structural element Q are optionally replaced by alkyl groups, alkoxy groups, halogen atoms or trifluoromethyl groups;

Y is methylene (—$CH_2$—);

n =0 or 1;

X is selected from the group consisting of —O—Z, —N—$(Z)_2$, —NH—Z, —O—C(=O)—Z, —C(=O)—O—Z, —O—C(=O)—NH—Z, —NH—C(=O)—O—Z, —NH—C(=O)—NH—Z, —C(=O)—NH—Z, —NH—C(=O)—Z, —C(=O)—N—$(Z)_2$, —N—(Z)—C(=O)—Z, —O—C(=O)—N(Z)—C(=O)—NH—Z, —NH—C(=O)—N(Z)—C(=O)—NH—Z, —N(C(=O)—NH—$Z)_2$, —C(=O)—N(Z)—C(=O)—NH—Z, —N(C(=O)—NH—Z)(C(=O)—Z), and —N(C(=O)—NH—Z)(C(=O)—O—Z), wherein the bond arranged on the left in each formula is closer to the structural element Q and wherein X is selected such that Z has a minimum number of atoms, Z is an organic radical having at least one carbon atom, and each Z may be the same or different, and o =2, 3, or 4, and (b) further constituents comprising (b-1) one or more different monomer(s) selected from the group consisting of (meth)acrylates, (b-2) one or more fillers, and (b-3) one or more photoinitiator(s) and/or one or more initiator(s) for chemical curing.

2. The dental composite material as claimed in claim 1, wherein Z is selected from the group consisting of:

a.) hydrocarbyl radicals [—$R_1$] wherein the number of carbon atoms is 1 to 30, and wherein the radicals may be linear or branched, and b.) hydrocarbyl ether radicals [(—$R_2$—O)$_q$—$R_3$] wherein the number of carbon atoms for $R_2$ is 2 to 6, and wherein the number of carbon atoms for $R_3$ is 1 to 20, and wherein $R_2$ and $R_3$ may be linear or branched and wherein q =1 to 15, and c.) hydrocarbyl ester radicals [—$R_4$—(C=O)—O—$R_5$] and [—$R_4$—O—(C=O)—$R_5$] wherein the number of carbon atoms for $R_4$ and $R_5$ is independently 1 to 15, and wherein $R_4$ and $R_5$ may be linear or branched and d.) hydrocarbyl ester radicals [—$R_4$—((C=O)—O—$R_5)_2$] and [—$R_4$—(O—(C=O)—$R_5)_2$], wherein the number of carbon atoms for $R_4$ and $R_5$ is independently 1 to 15 and wherein $R_4$ and $R_5$ may be linear or branched and e.) hydrocarbyl amino radicals [—$R_4$—N—$(R_5)_2$], wherein the number of carbon atoms for $R_4$ and $R_5$ is independently 1 to 15 and wherein $R_4$ and $R_5$ may be linear or branched, and f.) alkoxylated hydrocarbyl ester radicals [(—$R_2$—O)$_q$—$R_4$—(C=O)—O—$R_5$] and [(—$R_2$—O)$_q$—$R_4$—O—(C=O)—$R_5$], wherein the number of carbon atoms for $R_2$ is 2 to 6 and the number of carbon atoms for $R_4$ and $R_5$ is independently 1 to 15, wherein $R_2$, $R_4$, and $R_5$ may be linear or branched, and wherein q =1 to 15, and g.) substituted alkoxylated hydrocarbyl ester radicals [(—$R_2$—O)$_q$—$CH_2$—O—(C=O)—NH—$R_4$—(C=O)—O—$R_5$], wherein the number of carbon atoms for $R_2$ is 2 to 6 and the number of carbon atoms for $R_4$ and $R_5$ is independently 1 to 15, wherein $R_2$, $R_4$, and $R_5$ may be linear or branched, and wherein q =1 to 15, and h.) hydrocarbyl alcohol radicals having a terminal hydroxyl group [—$R_4$—OH], wherein the number of carbon atoms for $R_4$ is 1 to 15 and wherein $R_4$ may be linear or branched, and i.) hydrocarbyl alcohol radicals having one, two or more non-terminal/terminal hydroxyl group(s) and up to 30 carbon atoms, and j.) alkoxylated hydrocarbyl alcohol radicals [(—$R_2$—O)$_q$—$R_4$—OH], wherein the number of carbon atoms for $R_2$ is 2 to 6 and the number of carbon atoms for $R_4$ is 1 to 15, wherein $R_2$ and $R_4$ may be linear or branched, and wherein q =1 to 15 and k.) ketone radicals [—$R_6$—(C=O)—$R_7$] wherein the number of carbon atoms for $R_6$ is 1 to 30, and wherein the number of carbon atoms for $R_7$ is 1 to 30, and wherein $R_6$ and $R_7$ may be linear or branched.

3. The dental composite material as claimed in claim 1, wherein Z is selected from the group consisting of:

a.) hydrocarbyl radicals [—$R_1$] wherein the number of carbon atoms is 1 to 9 and wherein the radicals may be linear or branched, and b.) hydrocarbyl ether radicals [(—$R_2$—O)$_q$—$R_3$] wherein the number of carbon atoms for $R_2$ is 2 to 3 and wherein the number of carbon atoms for $R_3$ is 1 to 5 and wherein $R_2$ and $R_3$ may be linear or branched and wherein q =1 to 5, and c.) hydrocarbyl ester radicals [—$R_4$—(C=O)—O—$R_5$] and [—$R_4$—O—(C=O)—$R_5$] wherein the number of carbon atoms for $R_4$ and $R_5$ is independently 1 to 4 and wherein $R_4$ and $R_5$ may be linear or branched, and d.) hydrocarbyl ester radicals [—$R_4$—((C=O)—O—$R_5)_2$] and [—$R_4$—(O—(C=O)—$R_5)_2$], wherein the number of carbon atoms for $R_4$ and $R_5$ is independently 1 to 4 and wherein $R_4$ and $R_5$ may be linear or branched, and e.) hydrocarbyl amino radicals [—$R_4$-N-$(R_5)_2$], wherein the number of carbon atoms for $R_4$ and $R_5$ is independently 1 to 4 and wherein $R_4$ and $R_5$ may be linear or branched, and f.) alkoxylated hydrocarbyl ester radicals [(—$R_2$—O)$_q$—$R_4$—(C=O)—O—$R_5$] and [(—$R_2$—O)$_q$—$R_4$—O—(C=O)—$R_5$], wherein the number of carbon atoms for $R_2$ is 2 to 3 and the number of carbon atoms for $R_4$ and $R_5$ is independently 1 to 4, and wherein $R_2$, $R_4$, and $R_5$ may be linear or branched, and wherein q =1 to 5, and g.) substituted alkoxylated hydrocarbyl ester radicals [(=$R_2$—O)$_q$—$CH_2$—O—(C=O)—NH—$R_4$—(C=O)—O—$R_5$], wherein the number of carbon atoms for $R_2$ is 2 to 3 and the number of carbon atoms for $R_4$ and $R_5$ is independently 1 to 4, and wherein $R_2$, $R_4$, and $R_5$ may be linear or branched, and wherein q =1 to 5, and h.) hydrocarbyl alcohol radicals [—$R_4$—OH], wherein the number of carbon atoms for $R_4$ is 1 to 4 and wherein $R_4$ may be linear or branched, and i.) hydrocarbyl alcohol radicals having one, two or more non-terminal/terminal hydroxyl group(s) and up to 30 carbon atoms, and j.) alkoxylated hydrocarbyl alcohol radicals [(—$R_2$—O)$_q$—$R_4$—OH], wherein the number of carbon atoms for $R_2$ is 2 to 3 and the number of carbon atoms for $R_4$ is 1 to 4, and wherein $R_2$ and $R_4$ may be linear or branched, and wherein q =1 to 5, and k.) ketone radicals [—$R_6$—(C=O)—$R_7$] wherein the number of carbon atoms for $R_6$ is 1 to 10, and wherein the number of carbon atoms for $R_7$ is 1 and wherein $R_6$ may be linear or branched.

4. The dental composite material as claimed in claim 1, wherein none of the hydrogen atoms unsubstituted by $Y_n$-X substituents in the tricyclic structural element Q in the structure Q- [(Y)$_n$—X]$_o$, is substituted.

5. The dental composite material as claimed in claim 1, wherein Q is a tricyclo [5.2.1.0$^{2,6}$]decane radical or tricyclo [3.3.1.1$^{3,7}$]- decane radical.

6. The dental composite material as claimed in claim 1, wherein
constituent (a) is selected from the group consisting of 3(4),8(9)-bis(acyloxymethyl)-tricyclo[5.2.1.0$^{2,6}$]decane, alkoxylated 3(4),8(9) -bis(acyloxymethyl)tricyclo [5.2.1.0$^{2,6}$]decane, 1,3,5-triacyloxytricyclo[3.3.1.1$^{3,7}$] decane, alkoxylated triacyloxytricyclo[3.3.1.1$^{3,7}$] decane, tricyclo[5.2.1.0$^{2,6}$]decane-3(4),8(9)-dicarboxylic ester, the Michael-type adduct of 3(4),8(9)-bis(aminomethyl)tricyclo[5.2.1.0$^{2,6}$]decane and acrylic ester, 3(4),8(9)-bis(alkyloxymethyl)tricyclo[5.2.1.0$^{2,6}$] decane, alkoxylated 3(4),8(9)-bis(alkyloxymethyl)tricyclo-[5.2.1.0$^{2,6}$]decane, the addition product of 3(4),8 (9) -bis(hydroxymethyl)tricyclo[5.2.1.0$^{2,6}$]decane with isocyanate, the addition product of alkoxylated 3(4), 8(9) -bis(hydroxymethyl)tricyclo[5.2.1.0$^{2,6}$]decane with isocyanate, the addition product of 3(4),8(9)-bis (aminomethyl)tricyclo-[5.2.1.0$^{2,6}$]decane with isocyanate or the reaction product of 3(4),8(9)-bis(isocyanatomethyl)-tricyclo-[5.2.1.0$^{2,6}$]decane with amines, the addition product of alkoxylated 3(4),8(9)-bis -(aminomethyl)tricyclo[5.2.1.0$^{2,6}$]decane with isocyanate, the addition product of 3(4),8(9) -bis(isocyanatomethyl) tricyclo[5.2.1.0$^{2,6}$]decane with alcohol, the addition product of 3(4),8(9) -bis(isocyanatomethyl)tricyclo [5.2.1.0$^{2,6}$]decane with alkoxylated alcohol, the reaction product of 3(4),8(9)-bis(carbonyl halide)tricyclo [5.2.1.0$^{2,6}$]decane with an amine, or the reaction product of 3(4),8(9)-bis(carboxylic acid)tricyclo[5.2.1.0$^{2,6}$]decane with an isocyanate, the reaction product of 3(4),8 (9)-bis(isocyanatomethyl)tricyclo-[5.2.1.0$^{2,6}$]decane with an amino alcohol, the reaction product of 3(4),8(9)-bis(isocyanato-methyl)tricyclo[5.2.1.0$^{2,6}$]decane with an amino alcohol and subsequent alkoxylation of the resulting alcohol, the reaction product of 3(4),8(9) -bis (isocyanatomethyl)tricyclo[5.2.1.0$^{2,6}$]decane with an amino alcohol, subsequent alkoxylation of the resulting alcohol and reaction of this compound with carboxylic acid/carboxylic anhydride, the reaction product of 3(4), 8(9) -bis(aminomethyl)tricyclo[5.2.1.0$^{2,6}$]decane with alkyl halides, the reaction product of 3(4),8(9) -bis(aminomethyl)tricyclo[5.2.1.0$^{2,6}$]decane with acid halides, or the reaction product of 3(4),8(9) -bis(isocyanatomethyl)tricyclo[5.2.1.0$^{2,6}$]decane with carboxylic acids, the reaction product of 3(4),8(9) -bis(hydroxymethyl) tricyclo-[5.2.1.0$^{2,6}$]decane, or of alkoxylated 3(4),8(9)-bis(hydroxymethyl)tricyclo[5.2.1.0$^{2,6}$]decane, with fatty acids and the further reactions thereof, in the case of reaction products of unsaturated fatty acids, to give the corresponding ketones by the Wacker process, the reaction product of 3(4),8(9)-bis(aminomethyl)tricyclo [5.2.1.0$^{2,6}$]decane with epoxides and the further reaction product thereof with carboxylic acids, alkoxylated 3(4), 8(9) -bis(hydroxymethyl)tricyclo[5.2.1.0$^{2,6}$]decane and alkoxylated 3(4),8(9)-bis(aminomethyl)tricyclo-[5.2.1.0$^{2,6}$]decane,
constituent (b-1) is selected from the group consisting of 3(4),8(9)-bis((meth)acryloyloxy -methyl)tricyclo [5.2.1.0$^{2,6}$]decane, alkoxylated 3(4),8(9) -bis((meth) acryloyloxymethyl)tricyclo[5.2.1.0$^{2,6}$]decane, 2,3-bis ((meth)acryloyloxy-methyl)bicyclo[2.2.1]heptane, alkoxylated 2,3-bis((meth)acryloyloxymethyl)bicyclo [2.2.1]heptane, 1,3,5-tri(meth)acryloyloxytricyclo [3.3.1.1$^{3,7}$]decane, alkoxylated tri(meth)acryloyloxytricyclo[3.3.1.1$^{3,7}$]decane, (meth)acrylic esters of tricyclo [5.2.1.0$^{2,6}$]decane-3(4),8(9)-dimethanol, alkoxylated tricyclo[5.2.1.0$^{2,6}$]decane-3(4),8(9)-dimethanol, bicyclo[2.2.1]heptane-2,3-dimethanol, alkoxylated bicyclo [2.2.1]heptane-2,3-dimethanol, 1,3,5-adamantanetriol alkoxylated 1,3,5-adamantanetriol, with arrangement of urethane, urea, amide, allophanate, acylurea or biuret groups between the polyalicyclic structural element and the (meth)acrylic esters, ethylene glycol di(meth)acrylate, 1,6-hexanediol di (meth) acrylate (HEDMA), triethylene glycol di (meth) acrylate (TEDMA), 1,12-dodecanediol di (meth) acrylate, bisphenol A di (meth) acrylate, alkoxylated bisphenol A di (meth) acrylate, bisphenol B di (meth) acrylate, alkoxylated bisphenol B di (meth) acrylate, bisphenol C di (meth) acrylate, alkoxylated bisphenol C di (meth) acrylate, bisphenol F di (meth) acrylate, alkoxylated bisphenol F di (meth) acrylate, polyethylene glycol di (meth) acrylate, 7, 7, 9-trimethyl-4,13-dioxo-5,12-diazahexadecane 1,16-dioxydi (meth) acrylate (UDMA), butanediol di (meth) acrylate, tetraethylene glycol di (meth) acrylate, neopentyl glycol di (meth) acrylate, 2 -hydroxypropyl 1,3 -di (meth) acrylate, 3 -hydroxypropyl 1,2-di (meth) acrylate, pentaerythritol di (meth) acrylate, di (meth) acrylates of dihydroxy-methyltricyclo [5.2.1.0$^{2,6}$]decane, 2 -hydroxyethyl (meth) acrylate, 2 -hydroxypropyl (meth) acrylate, 3 -hydroxypropyl (meth) acrylate, 1,2 -dihydroxypropyl (meth) acrylate, 1,3 -dihydroxypropyl (meth) acrylate, 2,2 -bis [4-[3-(meth) acryloyloxy-2 -hydroxypropoxy]phenyl]propane (Bis-GMA), trimethylolpropane tri (meth) acrylate, trimethylol - ethane tri (meth) acrylate, pentaerythritol tri (meth) acrylate, trimethylolmethane tri (meth) -acrylate, pentaerythritol tetra (meth) acrylate, ditrimethylolpropane tetra (meth) acrylate, pentaerythritol hexa (meth) acrylate, butylene glycol di (meth) acrylate, propylene glycol di (meth) acrylate, nonanediol di (meth) acrylate, decanediol di (meth) acrylate, glyceryl mono (meth) acrylate, glyceryl di (meth) acrylate, trimethylolpropane mono (meth) acrylate, trimethylolpropane di (meth) acrylate, sorbitol mono-, di-, tri-, tetra- or penta (meth) acrylate, methyl (meth) acrylate, ethyl (meth) acrylate, propyl (meth) acrylate, butyl (meth) acrylate) hexyl (meth) acrylate, tetrahydrofurfuryl (meth) acrylate, lauryl (meth) acrylate, cyclohexyl (meth) acrylate, allyl (meth) acrylate, glycidyl (meth) acrylate, 2-ethoxyethyl (meth) acrylate, methoxy polyethylene glycol (meth) acrylate, isobornyl (meth)acrylate, 2-(N,N-dimethylamino)ethyl (meth) acrylate, N -methylol(meth)acrylamide, diacetone(meth)acrylamide, 2,2-bis[4-(meth) acryloyloxyphenyl]propane, 2,2-bis[4-(meth) acryloyloxyethoxyphenyl]propane, 2,2-bis[4-(meth) acryloyloxydiethoxyphenyl]propane, 2,2-bis[4-(meth) acryloyloxytriethoxyphenyl]propane, 2,2-bis[4-(meth) acryloyloxytetraethoxyphenyl]- propane, 2,2-bis[4-(meth)acryloyloxypentaethoxy-phenyl]propane, 2,2-bis[4-(meth)acryloyloxydi-propoxyphenyl]propane, 2,2-bis[4-(meth)acryloyl-oxyethoxyphenyl]-2-[4-(meth)acryloyloxydiethoxy -phenyl]propane, 2-[4-(meth)acryloyloxydiethoxy-phenyl]-2-[4-(meth)acryloyloxytriethoxyphenyl]propane, 2-[4-(meth) acryloyloxdipropoxyphenyl]-2-[4-(meth) acryloyloxytriethoxyphenyl]propane, 2,2-bis[4-meth) acryloyloxyisopropoxyphenyl]propane, hydroxypivalic acid neopentyl glycol di(meth)acrylate, acetoacetoxyethyl (meth)acrylate, polypropylene glycol di(meth) acrylate, glyceryl alkoxylate dimethacrylate, neopentyl glycol (meth)acrylate, N,N-(1,2-dihydroxyethylene) bis-acrylamide, 2,2-bis[4-(meth)acryloyloxy-pentaethoxyphenyl]propane, 2,2-bis[4-(meth) -acryloyloxy-polyethoxyphenyl]propane, diethylene glycol di(meth) acrylate, dipentaerythritol tetra-(meth)acrylate, dipentaerythritol hexa(meth)-acrylate, N,N-(2,2,4-trimethylhexamethylene)bis[2-(aminocarboxy)propane-1, 3-diol]tetra(meth)-acrylate, the condensation product of 3,(4) -(meth)acryloxymethyl-8,(9)-hydroxymethyltricyclo-[$5.2.1.0^{2,6}$]decane with dicarboxylic acids, 2-ethylhexyl (meth)acrylate, tridecyl (meth)acrylate, stearyl (meth)acrylate, cyclohexyl (meth)acrylate, benzyl (meth)acrylate, methoxy diethylene glycol (meth)acrylate, dicyclopentenyl (meth) acrylate, phenyl (meth) acrylate, pentaerythritol mono(meth)acrylate,di-pentaerythritol mono(meth)acrylate, caprolactone-modified tetrahydrofurfuryl (meth) acrylate, and light-curable monomers based on polysiloxanes, constituent (b-2) is selected from the group consisting of amorphous materials based on mixed oxides of $SiO_2$, $ZrO_2$ and/or $TiO_2$, microfine fillers such as fumed silica or precipitated silica, and macro- or mini-fillers such as quartz glass ceramic or glass powder, barium silicate glasses, barium fluorosilicate glasses, strontium silicate glasses, strontium borosilicate, Li/Al silicate glasses, barium glasses, calcium silicates, sodium aluminum silicates, fluoroaluminum silicate glasses, oxides of aluminum or silicon, zeolites, apatite, zirconium silicates, sparingly soluble metal salts such as barium sulfate or calcium fluoride, and X-ray-opaque fillers such as ytterbium fluoride, and nanoscale solid particles having a mean particle size of not more than 200 nm, and which are unagglomerated and/or unaggregated, and constituent (b-3) is selected from the group consisting of alpha-diketones, benzoin alkyl ethers, thioxanthones, benzophenones, acylphosphine oxides, acetophenones, ketals, titanocenes, sensitizing dyes, and borate salts and peroxides.

7. The dental composite material as claimed in claim 6, wherein the stoichiometry of the reactions of 3(4),8(9)-bis(hydroxymethyl)tricyclo[$5.2.1.0^{2,6}$]decane with isocyanate or of alkoxylated 3(4),8(9) -bis(hydroxymethyl)tricyclo[$5.2.1.0^{2,6}$]decane with isocyanate ranges from 1:1 to 1:2, such that the reaction products may comprise urethanes, allophanates or mixtures thereof in which the urethanes have not reacted fully to give the allophanates, 3(4),8(9)-bis(aminomethyl)tricyclo[$5.2.1.0^{2,6}$]decane with isocyanate or of alkoxylated 3(4),8(9) -bis(aminomethyl)tricyclo[$5.2.1.0^{2,6}$]decane with isocyanate ranges from 1:1 to 1:2, such that the reaction products may comprise ureas, biurets or mixtures thereof in which the ureas have not reacted fully to give the biurets, 3(4),8(9)-bis(carboxylic acid)tricyclo[$5.2.1.0^{2,6}$]decane with isocyanate ranges from 1:1 to 1:2, such that the reaction products may comprise amides, acylureas or mixtures thereof in which the amides have not reacted fully to give the acylureas, 3(4),8(9)-bis(carbonyl halide)tricyclo[$5.2.1.0^{2,6}$]decane with amine is 1:1 and gives an amide, and the second reaction stage to give the acylurea with a monoisocyanate is effected in a stoichiometry up to 1:1, such that the reaction product may comprise amides, acylureas or mixtures thereof, 3(4),8(9)-bis(isocyanatomethyl)tricyclo[$5.2.1.0^{2,6}$]decane with alcohol or with alkoxylated alcohol is 1:1 and gives a urethane, and the second reaction stage to give the allophanate with a monoisocyanate is effected in a stoichiometry up to 1:1, such that the reaction product may comprise urethanes, allophanates or mixtures thereof, 3(4),8(9)-bis(isocyanatomethyl)tricyclo[$5.2.1.0^{2,6}$]decane with amine is 1:1 and gives a urea, and the second reaction stage to give the biuret with a monoisocyanate is effected in a stoichiometry up to 1:1, such that the reaction product may comprise ureas, biurets or mixtures thereof, 3(4),8(9)-bis(isocyanatomethyl)tricyclo[$5.2.1.0^{2,6}$]decane with carboxylic acid is 1:1 and gives an amide, and the second reaction stage to give the acylurea with a monoisocyanate is effected in a stoichiometry up to 1:1, such that the reaction product may comprise amides, acylureas or mixtures thereof, and 3(4),8(9)-bis(aminomethyl)tricyclo[$5.2.1.0^{2,6}$]decane with acid halides is 1:1 and gives an amide, and the second reaction stage to give the acylurea with a monoisocyanate is effected in a stoichiometry up to 1:1, such that the reaction product may comprise amides, acylureas or mixtures thereof.

8. The dental composite material as claimed in claim 1, wherein
constituent (a) is 0.5 to 20% by weight,
constituent (b-1) is 5 to 90% by weight,
constituent (b-2) is 1 to 85% by weight, and
constituent (b-3) is 0.05 to 8% by weight.

9. The dental composite material as claimed in claim 1, wherein
constituent (a) is 2 to 10% by weight
constituent (b-1) is 25 to 80% by weight
constituent (b-2) is 20 to 75% by weight and
constituent (b-3) is 0.5 to 4% by weight.

10. The dental composite material as claimed in claim 6, comprising
(a) 2 to 10% by weight of a plasticizer selected from the group consisting of 3(4),8(9) -bis(acetyloxymethyl)tricyclo[$5.2.1.0^{2,6}$]decane, alkoxylated 3(4),8(9)-bis(acetyloxy-methyl)tricyclo[$5.2.1.0^{2,6}$]decane, 1,3,5-triacetyloxytricyclo[3.3.1.13,7]decane, alkoxylated triacetyloxytricyclo[$3.3.1.1^{3,7}$]decane, tricyclo [$5.2.1.0^{2,6}$]-decane-3(4),8(9)-dicarboxylic acid ethyl ester and the Michael -type adduct of 3(4),8(9)-bis(aminomethyl)tricyclo-[$5.2.1.0^{2,6}$]decane and methyl acrylate,
(b-1) 25 to 80% by weight of a free-radically curable monomer selected from the group consisting of 7,7,9-trimethyl-4,13-dioxo-5,12-diazahexadecane-1,16-dioxy di(meth)acrylate (UDMA), triethylene glycol di(meth)acrylate (TEDMA) and 3(4),8(9)-bis-(methacryloyloxymethyl)tricyclo[$5.2.1.0^{2,6}$]decane,
(b-2) 20 to 75% by weight of a filler selected from the group consisting of glass ceramic, silicas, X-ray-opaque fillers, and nanoscale fillers below 200 nm,
(b-3) 0.5 to 4% by weight of a photoinitiator selected from the group consisting of camphorquinone/amine and phosphine oxide, a chemical initiator selected from the group consisting of peroxide/amine and barbituric acid/barbituric acid derivatives in combination with heavy metal salts, and combinations thereof.

11. The dental composite material as claimed in claim 1, wherein constituent (b-2) is organically surface-modified.

12. The dental composite material as claimed in claim 11, wherein constituent (b-2) is silanized.

13. The dental composite material as claimed in claim 1, wherein the curable dental composite material is a two-component system, constituent (b-3) comprising a redox system comprising a reducing agent and an oxidizing agent, and the dental composite material being in the form of two spatially separate components in the form of pastes, and the reducing agent being present in the first component and the oxidizing agent in the second component, and constituents (a), (b-1), and (b-2), being present in the first and/or second component, and the pastes being present in mixing ratios of first component to second component in the ratio of 10:1 to 1:10.

14. The dental composite material as claimed in claim 1, which gives a relining material after curing, wherein the relining material has a flexural strength, measured according to ISO 4049, of more than 73 MPa.

15. The dental composite material as claimed in claim 1, which gives a temporary crown and bridge material after curing, wherein the temporary crown and bridge material gives a water solubility, measured according to ISO 4049, of less than 2.5 µg/mm$^3$.

16. A dental material obtainable by curing a dental composite material as claimed in claim 1.

17. A process for producing a dental material, comprising:
  a.) providing one or more constituents (a) and (b) as claimed in claim 1,
  b.) producing a mixture by mixing the constituents (a) and (b) provided,
  c.) curing the constituents, the curing being effected either chemically and/or with light induction and/or with thermal induction.

18. The process as claimed in claim 17, wherein the dental material is selected from the group consisting of a cured filling material, a core buildup material, a temporary crown and bridge material, a luting cement, a relining material, a dental material, a modeling material, a base material, a covering composition for gingiva protection, a prosthetic material, a material for a temporary supraconstruction for a dental implant or a core for a temporary supraconstruction, an inlay, an onlay, and a veneer.

19. The dental composite material as claimed in claim 1, further comprising a constituent selected from the group consisting of
  (b-4) one or more polymerization inhibitor(s),
  (b-5) one or more solvents,
  and combinations thereof.

20. The dental composite material as claimed in claim 19, wherein
  constituent (b-4) is selected from the group consisting of hydroquinone monomethyl ether, 2,6-di-tert-butyl-4-methylphenol, 2,2-diphenyl-1-picrylhydrazyl, galvinoxyl and triphenylmethyl radicals, 2,3,6,6-tetramethylpiperidinyl-1-oxyl radicals and derivatives thereof, and phenothiazine, and
  constituent (b-5) is selected from the group consisting of toluene, xylene, isooctane, acetone, butanone, methyl isobutyl ketone, ethyl acetate, butyl acetate, tetrahydrofuran, N-methylpyrrolidone, dimethylacetamide, dimethylformamide, ethanol, propanols, butanols, pentanols, hexanols, cyclohexanol, heptanols, octanols, nonanols, decanols, and cycloaliphatic or arylaliphatic alcohols.

21. The dental composite material as claimed in claim 19, wherein
constituent (b-4) is 0 to 1% by weight, and
constituent (b-5) is 0 to 85% by weight.

* * * * *